US012557865B2

(12) United States Patent
Davie et al.

(10) Patent No.: US 12,557,865 B2
(45) Date of Patent: Feb. 24, 2026

(54) SURGICAL HELMET INCLUDING AN ADJUSTMENT MECHANISM

(71) Applicant: Stryker Corporation, Kalamazoo, MI (US)

(72) Inventors: Daniel Davie, Kalamazoo, MI (US); Steve Krentz, Caledonia, MI (US); Blake Weimer, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 494 days.

(21) Appl. No.: 17/937,905

(22) Filed: Oct. 4, 2022

(65) Prior Publication Data

US 2023/0111620 A1 Apr. 13, 2023

Related U.S. Application Data

(60) Provisional application No. 63/254,304, filed on Oct. 11, 2021.

(51) Int. Cl.
*A42B 3/04* (2006.01)
*A42B 3/14* (2006.01)
(Continued)

(52) U.S. Cl.
CPC ................ *A42B 3/044* (2013.01); *A42B 3/14* (2013.01); *A42B 3/28* (2013.01); *A61B 90/35* (2016.02)

(58) Field of Classification Search
CPC ........... A61B 90/35; A42B 3/28; A42B 3/044; A42B 3/10; A42B 3/145; A42B 3/0433;
(Continued)

(56) References Cited

U.S. PATENT DOCUMENTS 4,724,546 A 2/1988 Cumbie, Jr.
7,222,374 B2 5/2007 Musal et al.
(Continued)

FOREIGN PATENT DOCUMENTS

FR 3060972 A1 * 6/2018 ......... A41D 13/1161
IT 202000009022 A1 10/2021
WO 2020086180 A1 4/2020

OTHER PUBLICATIONS

Machine-assisted English translation for IT 202000009022 A1 extracted from the espacenet.com database on Dec. 4, 2022, 12 pages.
(Continued)

*Primary Examiner* — Patrick J. Lynch
(74) *Attorney, Agent, or Firm* — Howard & Howard Attorneys PLLC

(57) ABSTRACT

A surgical apparel system including a surgical helmet to which a garment may mounted. The surgical helmet includes an electrically powered peripheral device, such as a ventilation assembly, and a headband for removably securing the surgical helmet to the head of a wearer. The headband comprises a rear a portion including opposing ends defining a contact point configured to contact the head of the wearer. The rear portion may also comprise a support member disposed between the opposing ends. The support member may be offset distally from the contact points such that the support member defines a void between the head of the wearer and the headband to allow the hair to collect between the head of the wearer and the support member.

17 Claims, 19 Drawing Sheets

(51) Int. Cl.
  *A42B 3/28* (2006.01)
  *A61B 90/35* (2016.01)
(58) Field of Classification Search
  CPC ....... A42B 3/0446; A42B 3/14; A62B 18/003;
          A62B 18/045; A62B 17/04; A41D
                    13/1218; A41D 13/1153
  See application file for complete search history.

(56) References Cited

U.S. PATENT DOCUMENTS

| | | | |
|---|---|---|---|
| 7,311,413 B1 * | 12/2007 | Barnes | A42B 3/044 |
| | | | 362/240 |
| 7,735,156 B2 | 6/2010 | VanDerWoude et al. | |
| 7,798,666 B2 | 9/2010 | Lehrl et al. | |
| 8,234,722 B2 | 8/2012 | VanDerWoude et al. | |
| 8,348,448 B2 | 1/2013 | Orozco et al. | |
| 8,407,818 B2 | 4/2013 | VanDerWoude et al. | |
| 8,850,624 B2 | 10/2014 | Gleason et al. | |
| 9,414,636 B2 | 8/2016 | Pietrzak | |
| 10,111,486 B2 * | 10/2018 | Gotti | A42B 3/08 |
| 10,548,363 B2 | 2/2020 | Pritz et al. | |
| D884,236 S | 5/2020 | Africa et al. | |
| 10,724,716 B2 | 7/2020 | Neeley et al. | |
| D901,737 S | 11/2020 | Neeley et al. | |
| 10,874,163 B2 | 12/2020 | VanDerWoude et al. | |
| 11,067,267 B2 | 7/2021 | Neeley et al. | |
| 11,090,516 B2 | 8/2021 | VanDerWoude et al. | |
| 11,147,333 B2 | 10/2021 | Wu | |
| 11,147,648 B2 | 10/2021 | Ferguson | |
| 11,197,507 B2 | 12/2021 | Ulmer et al. | |
| 11,284,655 B2 | 3/2022 | Pavalarajan et al. | |
| 11,291,265 B2 | 4/2022 | Jefferis et al. | |
| 2001/0032348 A1 * | 10/2001 | Diaz | A42B 3/286 |
| | | | 2/424 |
| 2002/0034073 A1 | 3/2002 | Halasz | |

| | | | |
|---|---|---|---|
| 2006/0213523 A1 * | 9/2006 | VanDerWoude | A41D 13/0025 |
| | | | 128/863 |
| 2008/0295229 A1 * | 12/2008 | Fang | A42B 3/145 |
| | | | 2/418 |
| 2010/0050324 A1 | 3/2010 | Musal | |
| 2011/0004979 A1 * | 1/2011 | VanDerWoude | A42B 3/322 |
| | | | 2/422 |
| 2011/0188236 A1 | 8/2011 | Eichelberger et al. | |
| 2012/0297520 A1 * | 11/2012 | Gleason | A42B 3/142 |
| | | | 2/181 |
| 2015/0107006 A1 * | 4/2015 | Chen | A42B 3/324 |
| | | | 2/418 |
| 2015/0208749 A1 | 7/2015 | Carroll | |
| 2016/0174648 A1 * | 6/2016 | Garneau | A42B 3/142 |
| | | | 2/421 |
| 2017/0347736 A1 | 12/2017 | Penner et al. | |
| 2018/0042330 A1 * | 2/2018 | Wu | A42B 3/225 |
| 2018/0368505 A1 * | 12/2018 | Kidman | A42B 3/042 |
| 2019/0029885 A1 * | 1/2019 | Seo | A42B 3/085 |
| 2020/0060359 A1 | 2/2020 | Jascomb et al. | |
| 2020/0300453 A1 | 9/2020 | Buhl | |
| 2020/0359718 A1 | 11/2020 | Jefferis et al. | |
| 2020/0405001 A1 * | 12/2020 | Ferguson | A42B 3/145 |
| 2021/0228919 A1 | 7/2021 | Rosati et al. | |
| 2021/0348751 A1 | 11/2021 | Neeley et al. | |
| 2022/0110381 A1 | 4/2022 | Jefferis et al. | |

OTHER PUBLICATIONS

Thi, "Vivi Infection Protection System Webpage", https://www. thigmbh.at/products/vivi/, 2011-2022, 14 pages.

Zimmer Biomet, "TotalShield II Surgical Helmet System Webpage", https://www.zimmerbiomet.com/medical-professionals/surgical-and-operating-room-solutions/product/totalshield-surgical-helmet-system. html, 2022, 7 pages.

* cited by examiner

SURGICAL HELMET INCLUDING AN ADJUSTMENT MECHANISM

RELATED APPLICATIONS

This application claims priority to and the benefit of U.S. Provisional Application No. 63/254,304, filed on Oct. 11, 2021, the entire contents of which are hereby incorporated by reference.

BACKGROUND

Surgical apparel systems are used in surgical procedures to provide a sterile barrier between the surgical personnel and the patient. Specifically, the traditional system includes a surgical helmet that supports a garment, such as a toga or a hood. This system is worn by medical/surgical personnel that want to establish the sterile barrier. The garment may include a transparent face shield. The helmet includes a peripheral device such as a ventilation unit that includes a fan. The ventilation unit draws air through the garment so the air is circulated around the wearer. This reduces both the amount of heat that is trapped within the garment and the amount of $CO_2$ that builds up in this space. It is further known to mount a light to the surgical helmet, which may be directed toward and illuminate the surgical site.

Often, surgical personnel wear surgical helmets for long durations. The fit and form of the surgical helmet play a large role in maintaining comfort for surgical personnel. To maintain a proper fit, a surgical helmet must be capable of accommodating varying head sizes and physical features of numerous individual surgical personnel. A surgical helmet assembly with features designed to overcome at least the aforementioned challenges is desired. These and other configurations, features, and advantages of the present disclosure will be apparent to those skilled in the art. The present disclosure is not to be limited to or by these configurations, features, and advantages

SUMMARY

The present disclosure relates generally to a surgical helmet assembly for mounting to a head of a user during surgical operations.

The present disclosure also provides a surgical helmet for use with a surgical garment configured to define a barrier between a wearer and an external environment. The surgical helmet also includes a headband including a front portion, a rear portion and a pair of opposed side portions connecting the front portion to the rear portion, the headband configured to encircle a head of the wearer; a ventilation assembly coupled to the headband, the ventilation assembly configured to draw air through the surgical garment and circulate it about the wearer. The helmet also includes where the rear portion may include: a base member for receiving an end of each of the pair of opposed side portions; a pair of contact surfaces configured to contact the head of the wearer, each of the pair of contact surfaces is slidably coupled to one of the side portions; and at least one support member disposed between each of the pair of contact surfaces and the base member, the support member configured to offset the opposing ends proximally from the base member such that the rear portion defines a void between the pair of contact surfaces and the base member of the rear portion of the headband to allow the hair to collect between the head of the wearer and the base member.

Implementations may include one or more of the following features. The surgical helmet may include an adjustment mechanism/control member disposed on the base member of the rear portion of the headband and configured to alter a circumference of the headband by moving each of the pair of opposed side portions relative to the base member of the rear portion. The combination of the front portion, the rear portion, and the pair of opposed side portions define a continuous headband. The pair of contact surfaces and the support member are formed as an integral member of the base member of the rear portion of the headband. The void may include a first void defined laterally between the support member of each of the pair of contact surfaces and a second void defined sagittally between the base member and each of the pair of contact surfaces. The surgical helmet may include: a shell, the shell coupled to the headband and configured to at least partially encircle the ventilation assembly; and a head lamp disposed on at least one of the shell or the headband and configured to project a beam of light distally in front of the face of the wearer of the surgical helmet. The surgical helmet may include a bracket coupled to the shell and configured to at least partially encircle the head lamp, the bracket shaped to assist with directing the beam of light from the head lamp distally and away from the wearer. The bracket may include a distal edge and opposing proximal edge, the distal edge configured to be positioned adjacent the surgical garment; and a flexible member extending between the proximal edge of the bracket and a housing of the head lamp, the flexible member configured to move with the head lamp to fill a portion of the void between the proximal edge of the bracket and the housing of the head lamp to prevent beam of light from head light from being directed and/or reflected toward the wearer. The surgical helmet may include a lever disposed on the shell, the lever coupled to the housing of the head lamp and manipulatable by the wearer to move the head lamp to direct the beam of light coming from the head lamp. The shell may include a plurality of coupling features configured to removably engage the front mounting feature of the front portion of the headband, the plurality of coupling features incrementally spaced along the shell to provide sagittal adjustment of the front portion of the headband relative to the shell. A rear portion of the shell may include a pair of posts extending away from a central portion of the shell that encircles the ventilation assembly, the posts spaced laterally from one another to define a void between the pair of posts; and where the void defined by the pair of posts and the void defined between the pair of contact surfaces of the rear portion of the headband are aligned vertically and configured to allow the hair of the wearer to collect between the head of the wearer and the base member of the rear portion of the headband without interference from the headband or the shell.

In another aspect, a headband of a surgical helmet including an electrically powered assembly. The headband also includes a front portion. The headband also includes a pair of opposed side portions. The headband also includes a rear portion connected to the front portion by the pair of opposed side portions, the combination of the front portion, the pair of opposed side portions, and the rear portion of the headband configured to encircle a head of the wearer, the rear portion may include: a base member for receiving an end of each of the pair of opposed side portions; an adjustment mechanism/control member disposed on the base member, the adjustment mechanism configured to extend and retract each of the pair of opposed side portions relative to the base member to alter a circumference of the headband; a pair of contact surface positioned on opposed sides of a midline of the headband extending between the front and rear portions and configured to contact the head of the wearer, each of the pair of contact surfaces slidably coupled to one of the side portions; and a support member disposed between the pair of contact surfaces and the base member, the support member configured to offset the pair of contact surfaces proximally from the base member such that the rear portion defines a void between the pair of contact surfaces and the base member to allow the hair to collect between the head of the wearer and the base member.

In another aspect, a method of adjusting a headband of a surgical helmet. The method of adjusting also includes manipulating a control member to adjust a circumference of the headband defined by the combination of the front portion, the pair of opposed side portions, the rear portion which results in each of the pair of contact surface sliding along one of opposed side portions as the support member maintains the spacing between the pair of contact surfaces and the base member to define a void that allows the hair of a wearer to collect between a head of the wearer and the base member without interference from the base member of the headband.

Other features and advantages of the embodiments of the present disclosure will be readily appreciated, as the same becomes better understood, after reading the subsequent description taken in conjunction with the accompanying drawings.

BRIEF DESCRIPTION OF THE DRAWINGS

Referring now to the drawings, example illustrations are shown in detail. Although the drawings represent schematic embodiments and/or example configurations, the drawings are not necessarily to scale and certain features may be exaggerated to better illustrate and explain an innovative aspect of an example configuration. Furthermore, the example illustrations described herein are not intended to be exhaustive or otherwise limiting or restricting to the precise form and configuration shown in the drawings and disclosed in the following detailed description.

Advantages of the present disclosure will be readily appreciated as the same becomes better understood by reference to the following detailed description when considered in connection with the accompanying drawings.

DETAILED DESCRIPTION

Maintaining a reliable barrier between a healthcare provider and a patient to prevent the exchange and/or transfer of particles or foreign material during a medical procedure or examination is of the utmost importance. During medical and surgical procedures, a healthcare provider may wear an assembly known as a surgical apparel system, such as the surgical apparel system 10 illustrated in FIG. 1A.

Figure 1A:
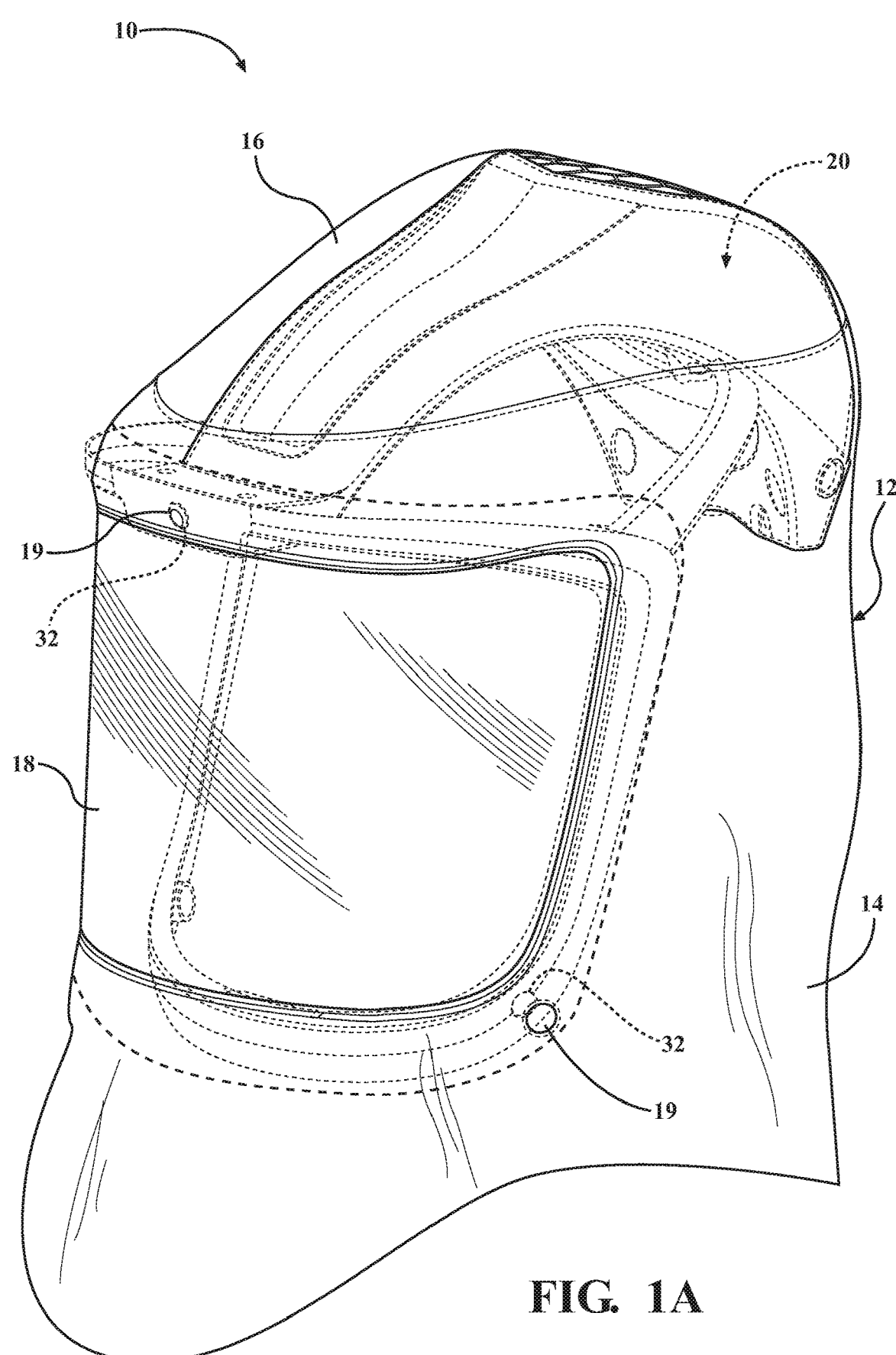
FIG. 1A is a perspective view of a first configuration of a surgical apparel system that includes a medical garment and a surgical helmet, with the surgical helmet shown in phantom.

Referring again to FIGS. 1A and 1B, an example configuration of the surgical apparel system 10 is described in detail. The system may include a surgical garment 12 and a surgical helmet 20. The surgical garment 12, which may also be referred to as a medical garment, may be configured as a hood or a toga to be placed over the surgical helmet 20. In the hood configuration, as is illustrated in FIG. 1A, the surgical garment 12 may be positioned over the surgical helmet 20 and configured to encompass the surgical helmet 20 and, correspondingly, the head of the person wearing the surgical apparel system 10, thereby covering the wearer's face and back of the head. Alternatively, if the surgical garment 12 were configured as a toga, the toga may be positioned over the surgical helmet 20 and configured to encompass the surgical helmet 20 and, correspondingly, the head, arms, shoulders, and torso of the person wearing the surgical apparel system 10. To place the surgical garment 12 over the surgical helmet 20, the surgical garment 12 will typically be turned inside out as the face shield 18 is aligned and affixed to the surgical helmet 20 in the manner described below. Once the face shield 18 is positioned relative to the surgical helmet 20, the remainder of the surgical fabric 14 will typically be pulled over the wearer's head to cover the exposed components of the surgical helmet 20 and the wearer's head.

Accordingly, the surgical garment 12 may also be configured for attachment to a surgical helmet 20. The surgical garment 12 is configured to provide a barrier, such as a microbial barrier, between the wearer and the surrounding environment. The barrier created by the surgical garment 12 may benefit both the wearer and the patient. The barrier provided by the surgical garment 12 may substantially eliminate the likelihood that the wearer may come into contact with fluid or solid particles of matter from the patient that may be generated during the course of a surgical procedure. The barrier may substantially prevent the transfer of any foreign particles emitted by the wearer from being transferred to the patient during the surgical procedure.

Referring to FIG. 1A, the surgical garment 12 may include a surgical fabric 14, which may also be referred to as a shell, configured to cover the surgical helmet 20 and at least a portion of the head of the wearer. The surgical garment 12 may be configured as a hood, as illustrated in FIG. 1A. It will be understood that a hood refers to a surgical garment 12 that covers the head and likely only extends a short distance below the neck when worn by the wearer. However, while not illustrated in the figures, it is further contemplated that the surgical garment 12 may be configured as a toga, a shirt, or a jacket. It will be understood that a toga 12 refers to a surgical garment 12 that covers the head in the same manner as a hood and extends to at least the waist when worn by the wearer.

The surgical garment 12 may be manufactured from any suitable surgical fabric 14 or combinations of fabrics to help repel and/or absorb water, debris and other contaminants. The surgical fabric 14 may include multiple layers. One such layer may be a microporous film that allows gas to pass through the fabric while still maintaining the microbial barrier.

It is further contemplated that the surgical garment 12 may be constructed of multiple different fabrics coupled to one another to define the barrier. For example, the surgical garment 12 may be primarily constructed from a barrier surgical fabric 14 and a filter fabric 16. The filter fabric 16 may be more permeable, and hence more breathable, than the barrier surgical fabric 14 described above. The filter fabric 16 may be located in an area with a reduced risk of having a microbial particle cross the barrier, such as above the wearer's head or proximate to the crown of the wearer's head, and configured to aid in the circulation of air through the barrier. The barrier surgical fabric 14 may be attached to the filter fabric 16 using any suitable means, such as adhesive, sewing, welding, or a combination thereof.

As illustrated in FIG. 1A, the surgical garment 12 may further comprise a face shield 18. The face shield 18 portion of the surgical garment 12 allows the wearer to see through the barrier provided by the surgical garment 12. The face shield 18 is generally a sheet-like structure and may have a thickness of approximately 1 mm or less. The face shield 18 may be mounted and/or attached to an opening or cut-out formed in the surgical fabric 14 of the surgical garment 12. The surgical fabric 14 may be attached around the periphery or edge of the face shield 18 by sewing, snaps, hook and loop, adhesive, welding, or combinations thereof. The face shield 18 may be constructed from a transparent material, such as a polycarbonate. One such polycarbonate is sold under the trademark LEXAN™ by Sabic. The face shield 18 of the surgical garment 12 may also be tinted to protect the wearer's eyes from heightened exposure to bright lights. Furthermore, the face shield 18 may be flexible such that the face shield 18 may be curved to accommodate different head sizes as will be described below.

The surgical garment 12 may also include one or more attachment elements 19 positioned about the surgical garment 12. The attachment elements 19 may also be referred to as a garment fastener or a second member. The attachment elements 19 are configured to releasably secure the surgical garment 12 to the surgical helmet 20. The attachment elements 19 may take any suitable form, and may comprise metal tacks, rivets, buttons, magnets, hook and loop, snaps, or similar types of fasteners, alone or in combination. As illustrated in FIG. 1A, the attachment elements 19 may be mounted to the face shield 18 of the surgical garment 12 so as to extend inwardly from the wearer side of the face shield 18. While not illustrated in the figures, it is also contemplated that the attachment elements 19 may be positioned at any other position or location about the surgical garment 12, including being mounted to the barrier surgical fabric 14 and/or the filtration fabric 16. The attachment elements 19 may be mounted to the face shield 18 and/or fabric(s) 14, 16 via an adhesive, rivet, snap, similar mounting device, or combination thereof.

Figure 1B:
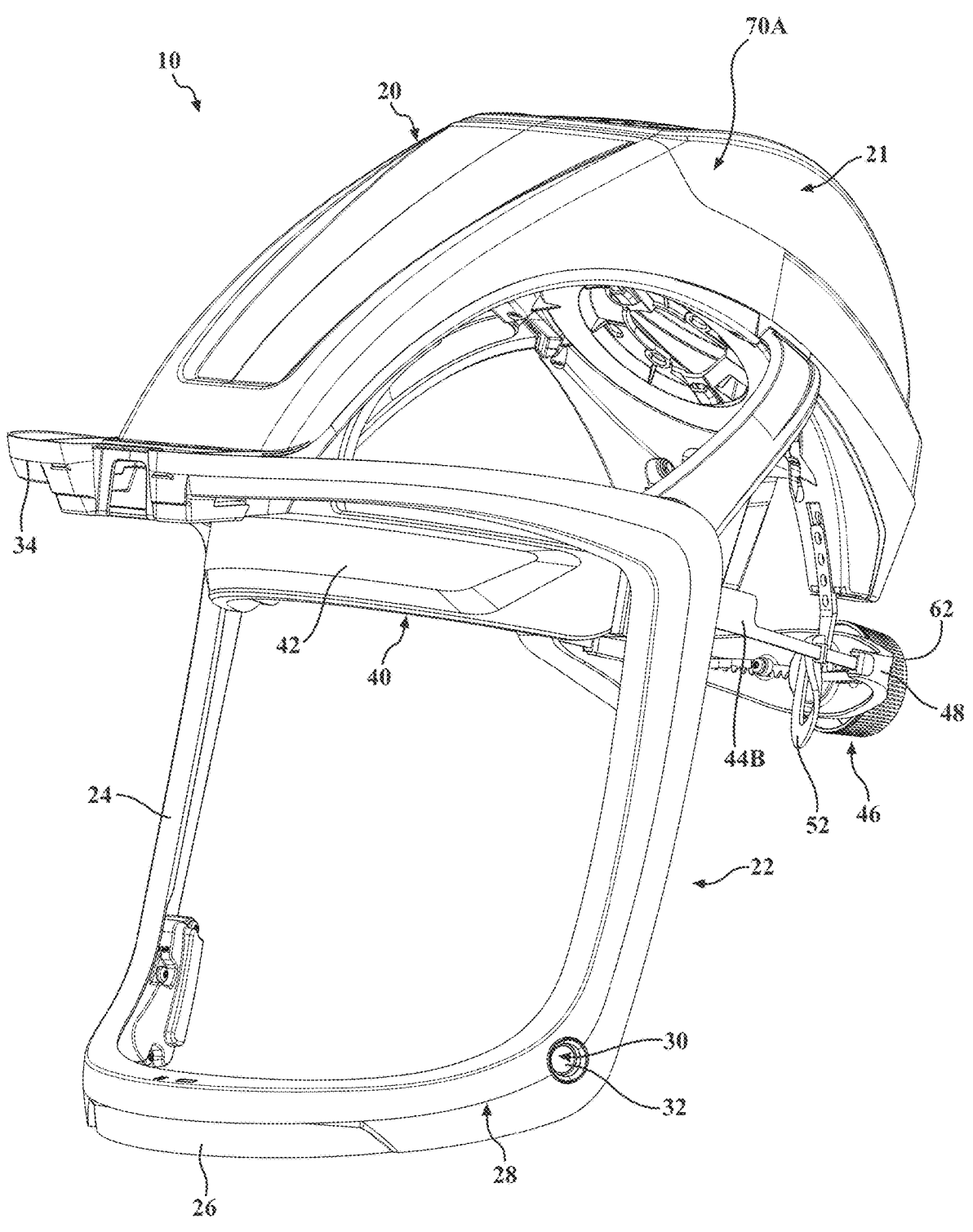
FIG. 1B is a perspective view of the surgical helmet of the surgical apparel system of FIG. 1A, the surgical helmet including a shell, a headband, and a face frame.

Referring to FIGS. 1B, an example configuration of the surgical helmet 20 that may be utilized as part of the surgical apparel system 10 is illustrated. The surgical helmet 20 illustrated in FIG. 1B includes a headband 40. The headband 40 may be configured to encircle the wearer's head and support the surgical helmet 20. The headband 40 may be constructed from a generally flexible or pliable material, allowing the headband 40 to conform to general shape of the wearer's head.

The headband 40 may comprise a rear portion 46 that includes a headband control assembly configured to adjust the size/shape of the headband 40. The rear portion 46 may comprise a control member 62 that is manipulatable by the wearer to adjust the size of the headband 40. For example, as illustrated in FIG. 1B, the control member 62 may comprise a rotatable knob or lever. When the wearer rotates the control member 62 in one direction, the headband control assembly 38 may be configured to reduce the size, i.e., the circumference, of the headband 40. Alternatively, when the wearer rotates the control member 62 in the opposite direction, the rear portion 46, which may also be referred to as a control assembly, may be configured to increase the size, i.e., the circumference, of the headband 62. This allows for the headband 40 of the surgical helmet 20 to be adjusted and/or customized to securely fit on a particular individual's head irrespective of the individual's head size and/or shape.

The surgical helmet 20 further includes a housing 21 that is supported by and located above the headband 40. The housing may also be referred to as a shell 21. The housing 21 may be configured in an arcuate shape to fit over the head of the individual wearing the surgical apparel system 10. Other helmet designs are contemplated. Many portions of the housing 21 may be formed to define voids, or open interior spaces. For example, the housing 21 may comprise a center void. The center void may be located toward the rear of the housing 21. There may be an intake opening or aperture in the top portion of the housing 21 to provide access to the center void. The housing 21 may also include additional voids, such as a front void proximate to the front of the housing 21 and a rear void proximate to the rear of the housing 21. The additional voids may be configured to form duct-like structures or passageways within the housing 21. The additional voids may even be interconnected to the center void.

The surgical helmet 20 may include one or more electrically powered peripheral devices 70, including but not limited to, a ventilation assembly 70A, a light 70B, a camera, microphone or other communication device, cooling device, or combinations thereof. These devices may be mounted to and/or attached at various locations and orientations relative to the surgical helmet 20. Each of the peripheral devices 70 may be configured to receive commands that affect the operating state of the corresponding peripheral device. For example, each of the peripheral devices 70 can receive on/off commands. Alternatively, the peripheral devices 70 may receive commands that change one or more settings of the peripheral devices 70. Such configurations allow the wearer of the surgical helmet 20 to control the operating state of the various peripheral devices 70 during the surgical procedure. In one specific example, when the peripheral device is a ventilation assembly 70A, the ventilation assembly 70A may be configured to receive various commands to control the actuation and/or adjust the speed of the fan in the ventilation assembly 70A. Alternatively, when the peripheral device 70 is a cooling device, the cooling device may be configured to receive commands to control the intensity of the cooling output provided by the cooling strip. When the peripheral device 70 is a microphone, the microphone may be configured to receive commands to control the volume of the audible signal produced by the microphone. When the peripheral device 70 is a light 70B, the light 70B may be configured to receive commands to control the direction and/or intensity of light emitted. The peripheral devices 70 may of course be configured to be responsive to other types of commands that control the operation of the peripheral device 70.

Figure 2A:
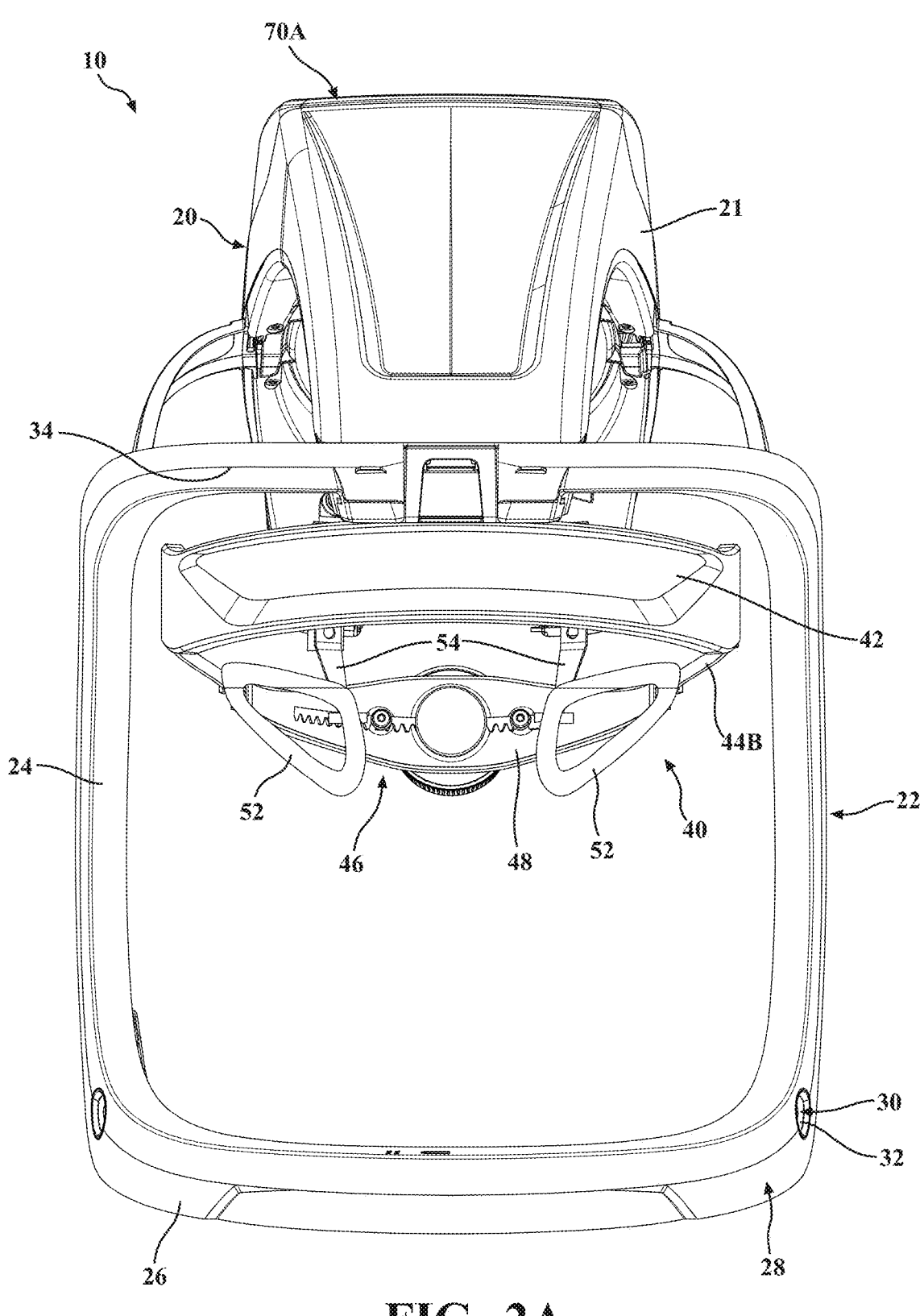
FIG. 2A is a front view of the surgical helmet of FIG. 1B, the headband and shell configured to define various helmet adjustment features.

The surgical helmet 20 may include a face frame 22 coupled to the shell 21 and positioned in front of the wearers face. The face frame 22 may include a top beam 34 and a chin bar 24, 26. The top beam 34 may be coupled to the front portion of the surgical helmet 20, and the chin bar 24, 26 may extend downwardly from the top beam 34. The chin bar 24, 26 may comprise a pair of posts 24 that extend away from the top beam 34. The pair of posts 24 may be coupled to the top beam 34, wherein the top beam 34 is configured to extend across the front of the surgical helmet 20. For example, as illustrated in FIG. 2A, the posts 24 may be connected to opposing ends of the top beam 34. The chin bar 24, 26 may be constructed from a generally flexible or pliable material.

The chin bar 24, 26 may further comprise a bottom beam 26 that may extend between the opposed free ends of the posts 24. The chin bar 24, 26 is formed so that the bottom beam 26 is located below and slightly forward of the chin of the person wearing the surgical helmet 20. The bottom beam 26 may be bowed outwardly from the free ends of posts 24. The chin bar 24, 26 may extend outwardly from the top beam 34 such that the chin bar 24, 26 is positioned forward of and generally encircles the face of the wearer when the surgical helmet 20 is secured to the wearer's head. Collectively, the combination of the top beam 34, the posts 24, and the bottom beam 26 may be referred to as the face frame 22, as they generally define an opening positioned in front of the wearer's face when the surgical helmet is positioned on top of the wearer's head.

A plurality of coupling members 30 may be mounted to or dispose on the face frame 22. The coupling members 30 comprise magnetic material and are configured to align and/or attach the face shield 18 of the surgical garment 12 to the surgical helmet 20. Each coupling member 30 may be positioned on the face frame 22 proximate to the opposed posts 24 and/or adjacent opposing ends of the bottom beam 24. Alternatively, the coupling members 30 of the surgical helmet 20 could be arranged or otherwise configured in any suitable way to cooperate with the complementary attachment elements 19 of surgical garment 12 to releasably secure the surgical garment 12 to the surgical helmet 20. For example, as illustrated in FIG. 1A, the coupling member(s) 30 may be positioned on the face frame 22 at opposing ends of the lower beam 26 proximate where each of the posts 24 connects to the lower beam 26. The coupling member(s) 30 may also be disposed on the upper beam 34 of the face frame 22. The surgical helmet 20 and/or the face frame 22 may be configured to have any number of coupling members 30. For example, the surgical helmet 20 may utilize two coupling members 30. Alternatively, it is also contemplated that the surgical helmet 20 may be configured such that the face frame 22 comprises a single coupling member 30 or, in other configurations, three or more coupling members 30 may be spaced about the chin bar 24, 26 and/or top beam 34. It is contemplated that other types of coupling members 30 may be used in place of and/or in addition to those comprising magnetic materials, such as with a hook and loop fasteners, snaps, coupling members comprising ferromagnetic material, or similar type fasteners. Other configurations are contemplated.

It is further contemplated that the face frame 22 may optionally be configured to define one or more recesses 32. The face frame 22 may comprise a recess 32 configured to receive the coupling feature 30. For example, as illustrated in FIG. 1B, the coupling member 30 may be positioned within the recess 32 defined by the face frame 22, such that the distal surface of the coupling member 30 is positioned proximally to a distal surface 28 of the face frame 22.

Referring to FIGS. 2A through 5, an example configuration of the surgical helmet 20 including a headband 40 with a hair management system is illustrated. An example configuration of the headband 40 is further illustrated in FIGS. 6 through 9 separated from the helmet 20. The headband 40 includes a front portion 42, rear portion 46, and pair of opposing side portions 44A, 44B connecting the front portion 42 to the rear portion 46. The front portion 42 may be formed from a soft and/or flexible material such as a foam padding or plastic strap configured to form to the wearer's head when the helmet is worn. This can provide both adjustably across multiple wearer's and provide comfort to the wearer as the headband 40 supports the helmet 20 about the wearer's head.

The front portion 42 of the headband 40 may also comprise a strap, bracket, strip of material or similar member for removably coupling the front portion 42 of the headband 40 to the shell 21 of the surgical helmet 20. The strap 64 may comprise an aperture 66 or similar coupling feature corresponding to a reciprocal coupling feature of the helmet 20, such as post or post or pin configured to create a snap fit with the aperture 66 of the strap 64.

The side portion(s) 44A, 44B may be formed from a generally pliable and/or flexible material such as a plastic polymer. The side portions 44A, 44B may define a strap that connects the front portion 42 to the rear portion 46. The side portions 44A, 44B may further be formed to define teeth or a similar adjustment feature that allows for the circumference of the headband 40 to be adjusted to fit the wearer's head. For example, as illustrated in FIGS. 6 through 9, the side portions 44A, 44B may define teeth that interact a gear of the rear portion 46 of the headband 40. The rear portion 46 may be configured such that the wearer may manipulate the control member 62 to control the gear, which in turn manipulates the position of one or both of the side portions 44A, 44B relative to the rear portion. For example, rotating the control member 62 in one direction may cause the gear of the rear portion 46 to engage the teeth of the side portion(s) 44A, 44B to extend the side portions away from the rear portion 46 and increasing the circumference of the headband 40. Alternatively, rotating the control member 62 in the opposite direction may cause the gear of the rear portion 46 to engage the teeth of the side portion(s) 44A, 44B to retract the side portions 44A, 44B toward the rear portion 46 and decrease the circumference of the headband 40. In another configuration of the headband 40, the side portion(s) 44A, 44B may be formed from a stretchable material that allows the headband 40 to stretch to fit the wearer's head. As illustrated in the figures, the front portion 42 and rear portion 46 are shown as separable components coupled to one another, however, it is further contemplated that the front portion 42 and the side portion(s) 44A, 44B may be constructed a single or unitary piece that is coupled to the rear portion 46.

The rear portion 46 may comprise a base member 48 and one or more contact surfaces 52A, 52B. The contact surfaces 52 may be connected to the base member 48 by a support member 50. The contact surfaces 52 may be shaped and/or positioned to contact the head of the wearer. The contact surfaces may also comprise a bracket 56A, 56B. A bracket 56A, 56B of each of the contact surfaces 52A, 52B may at least partially encircle one of the side portions 44A, 44B. The bracket 56A, 56B may be configured to allow the respective side portion 44A, 44B to slide within the respective bracket 56A, 56B allowing the bracket 56A, 56B to slidably move along the length of the side portion 44A, 44B The support member 50 of the rear portion 46 may be formed from a generally rigid bracket, bar, brace, shaft, rib, or the like configured to space the contact surface(s) 52A, 52B from the base 48. The support member 50 may be a separably coupled to one or both of the contact surface(s) 52A, 52B or the base 48. Alternatively, the support member 50 may be a unitarily formed with one or both of the contact surface(s) 52A, 52B and the base 48. The contact surfaces 52 and the support member 50 may be arranged to define a void 60 between the contact surface 52A, 52B and the base 48 of the rear portion 46. For example, the void 60 defined by the support member(s) 50 between the contact surface 52A, 52B and the base 48 may laterally space the base 48 from the head of the wearer to allow hair worn at the back of the wearers head, such as in a ponytail, to fit and/or fall between the wearer's head and the base 48 of the rear portion 46.

Figure 2B:
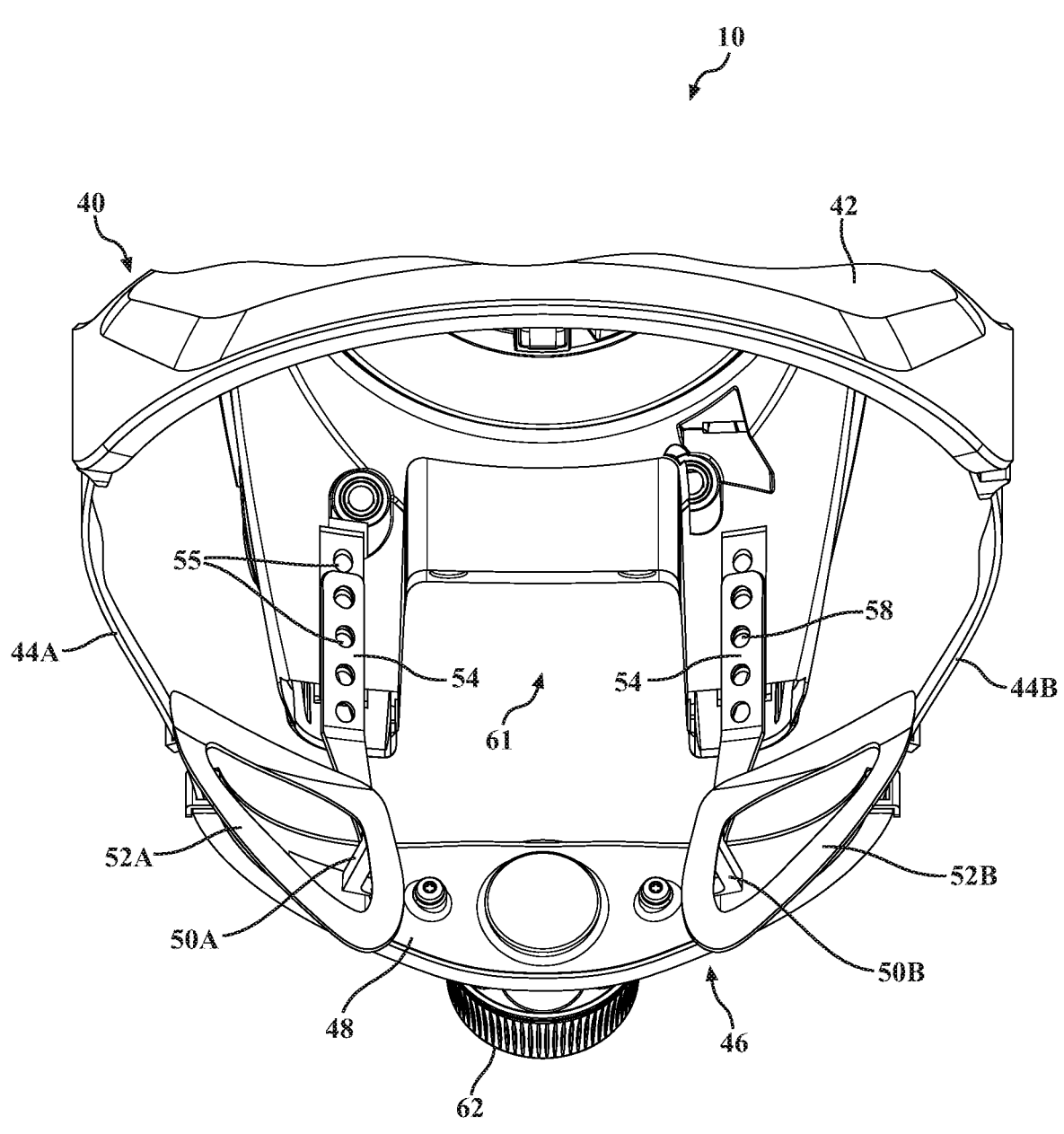
FIG. 2B is a zoomed front view of the surgical helmet of FIG. 2A illustrating the one example connection between the headband and surgical helmet.
Figure 3:
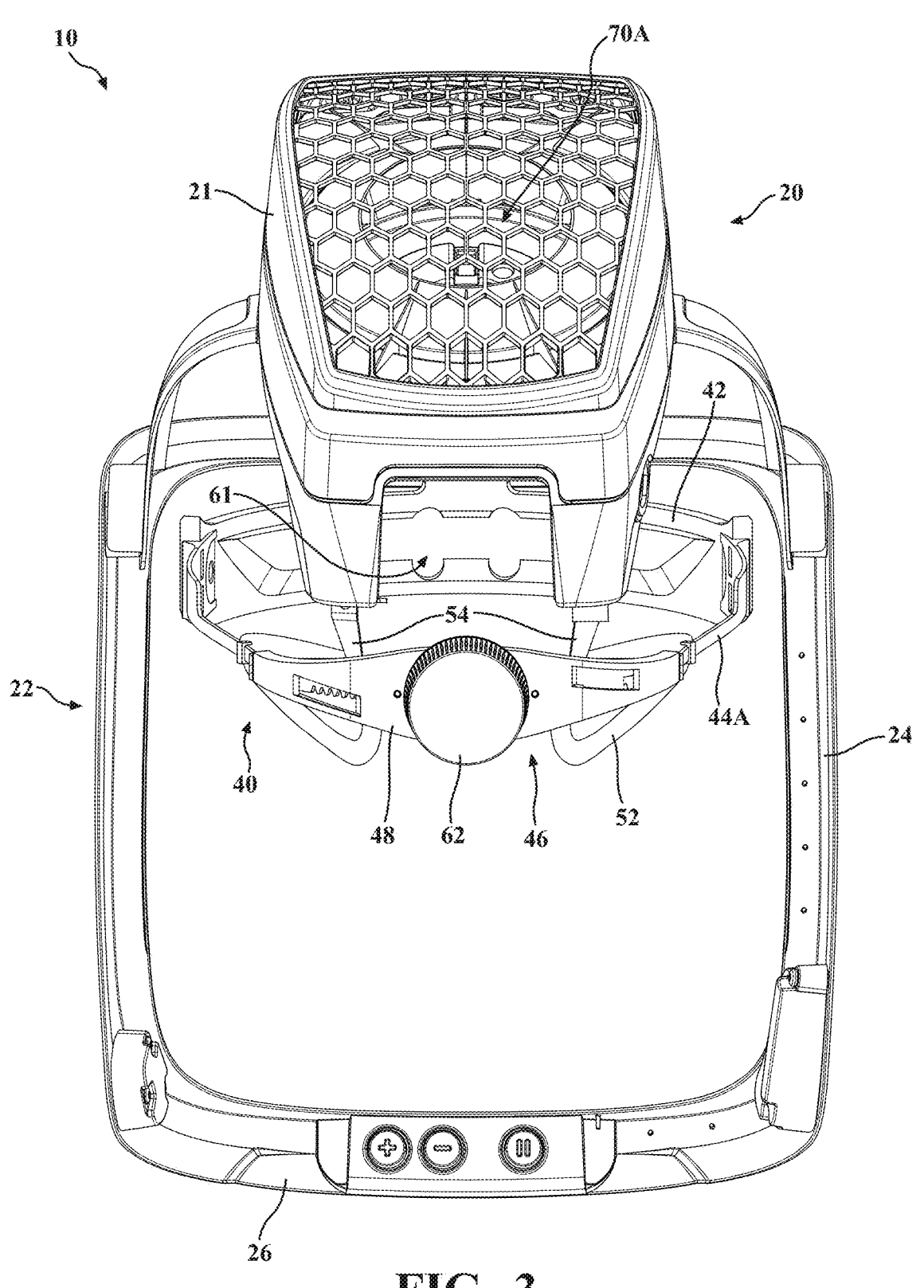
FIG. 3 is a rear view of the surgical helmet of FIG. 2A, including the headband and shell configured to define various helmet adjustment features.
Figure 4:
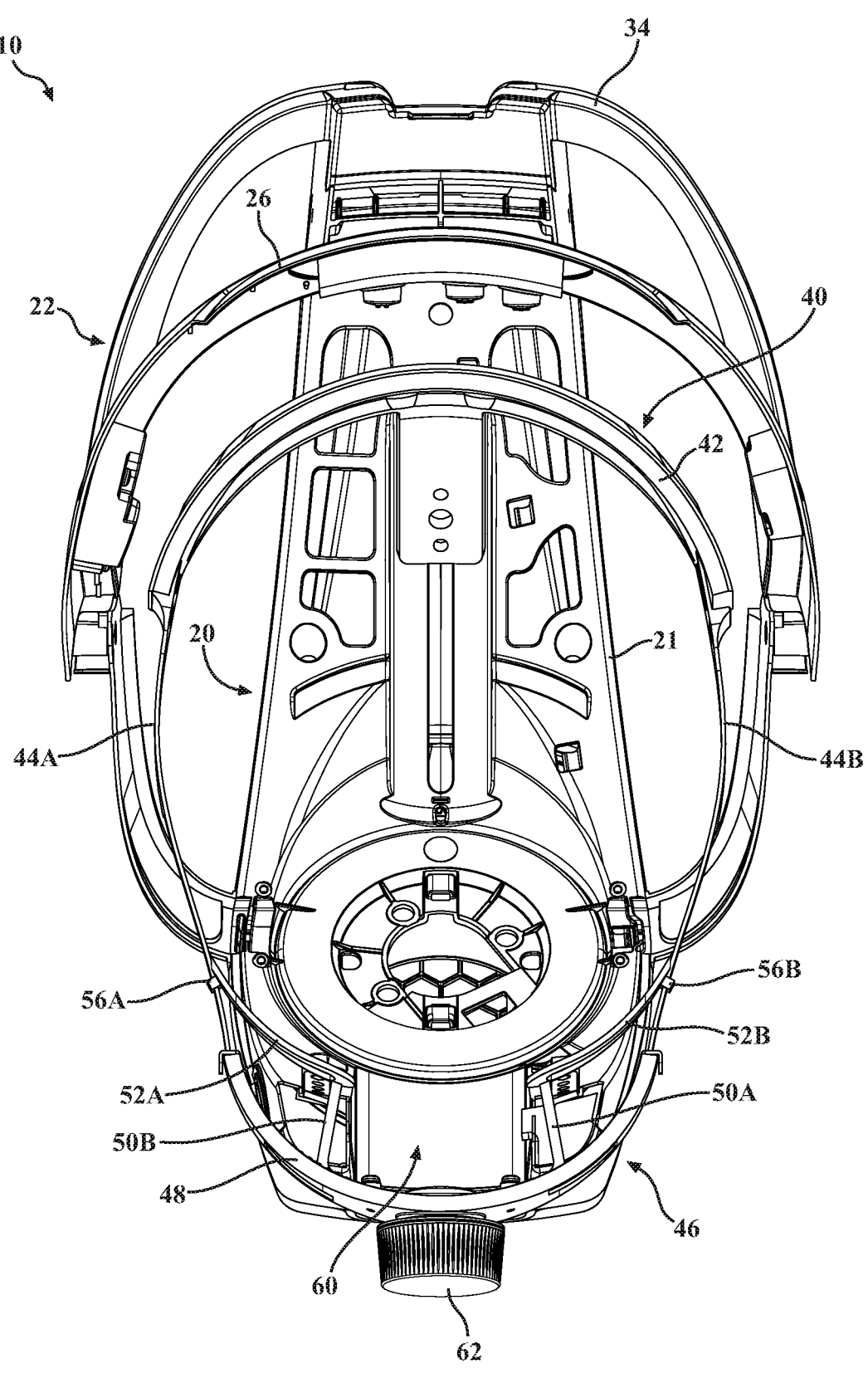
FIG. 4 is a bottom view of the surgical helmet of FIG. 2A, including the headband and shell configured to define various helmet adjustment features.
Figure 5:
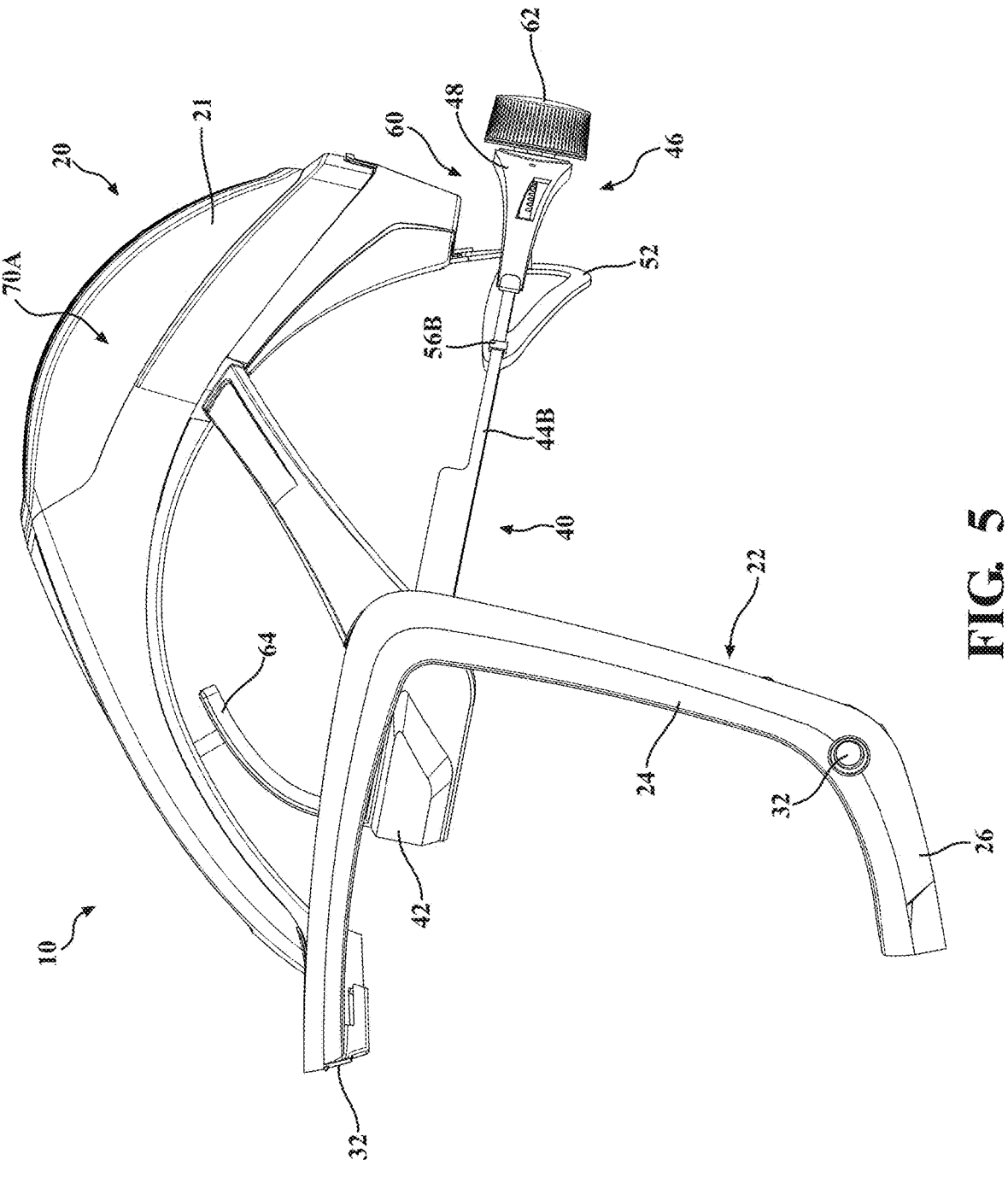
FIG. 5 is a side view of the surgical helmet of FIG. 2A, including the headband and shell configured to define various helmet adjustment features.
Figure 6:
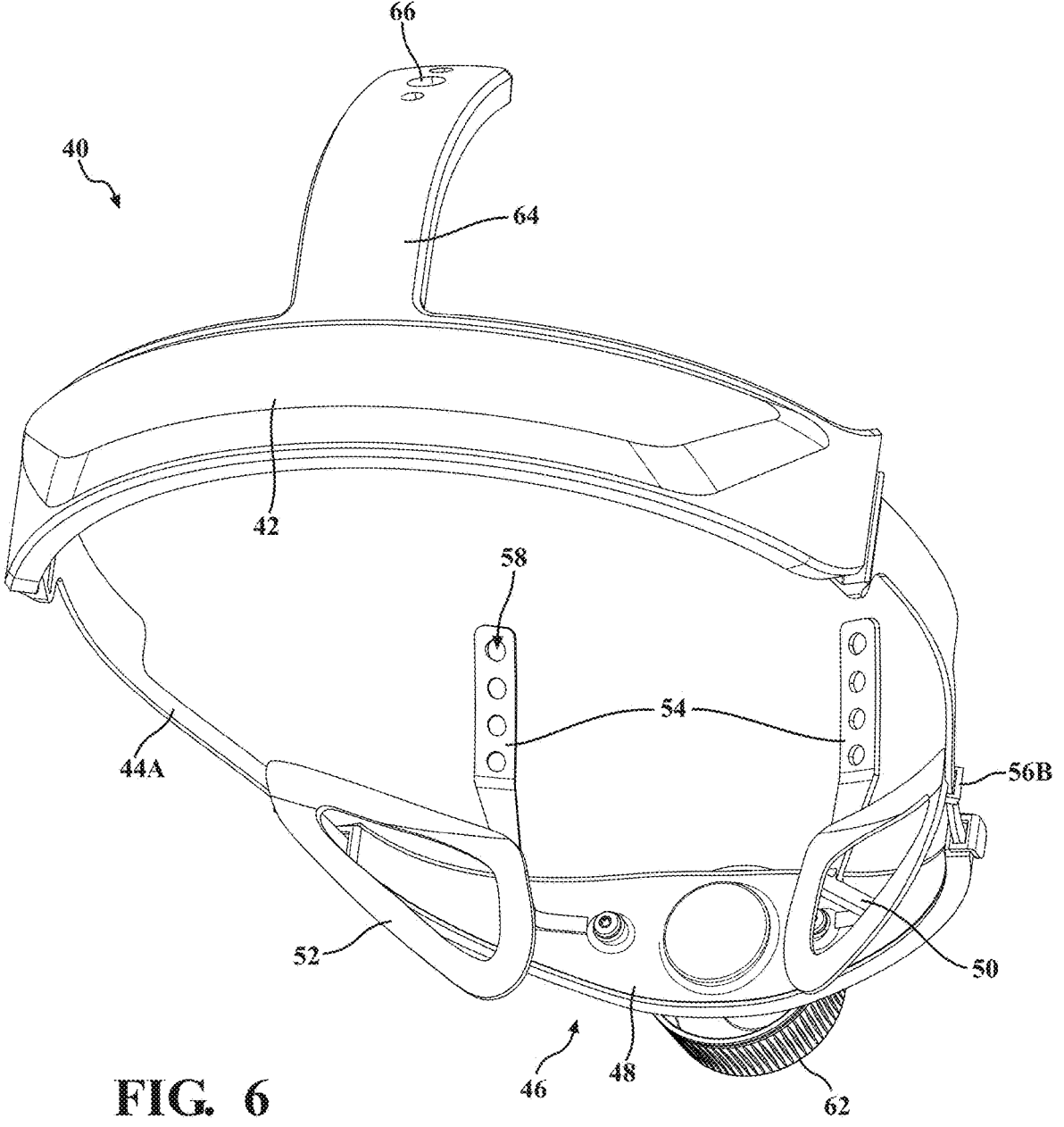
FIG. 6 is a perspective view of a headband of a surgical helmet, the headband including various helmet adjustment features.
Figure 7:
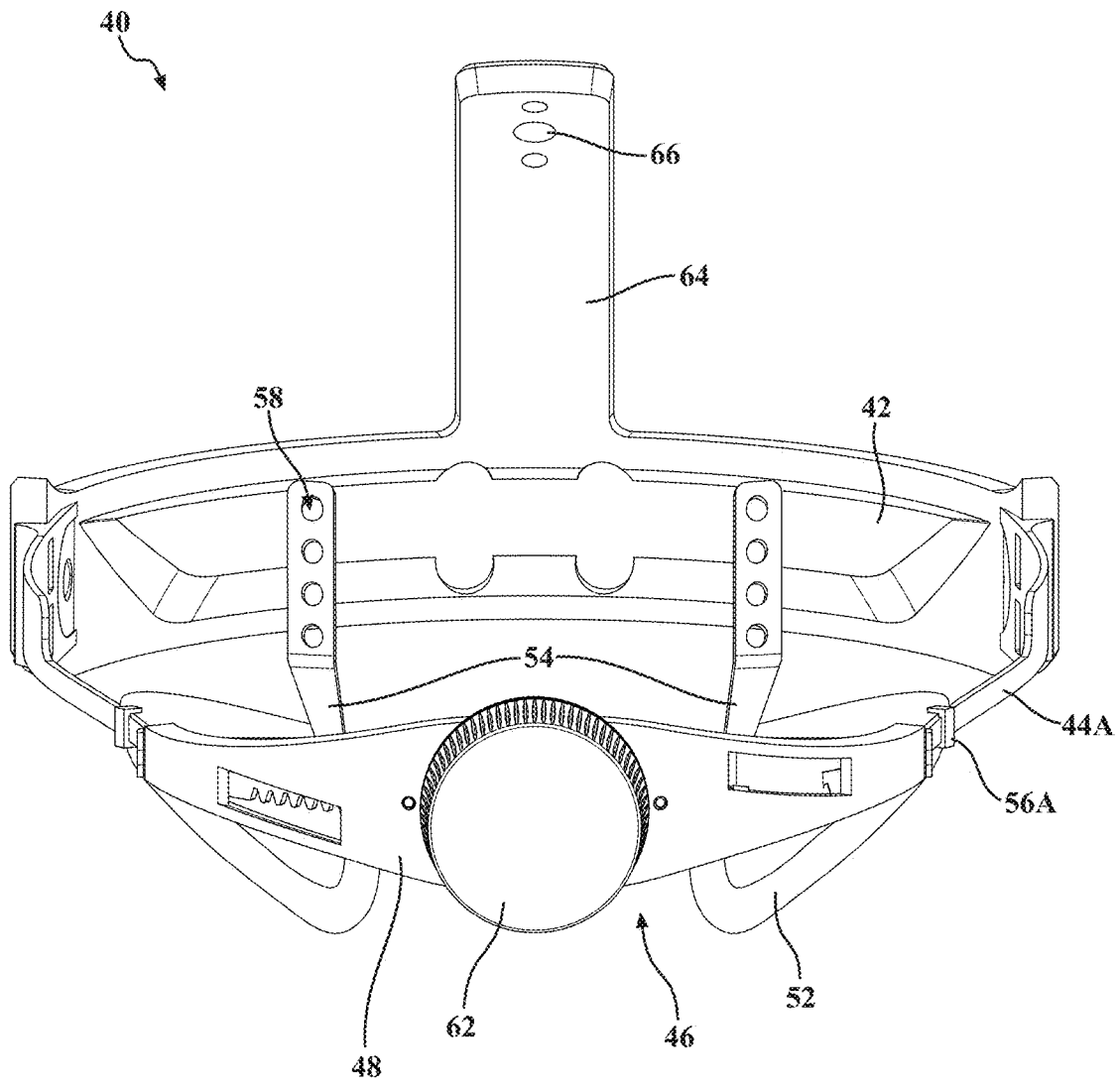
FIG. 7 is a rear view of the headband of FIG. 6.
Figure 8:
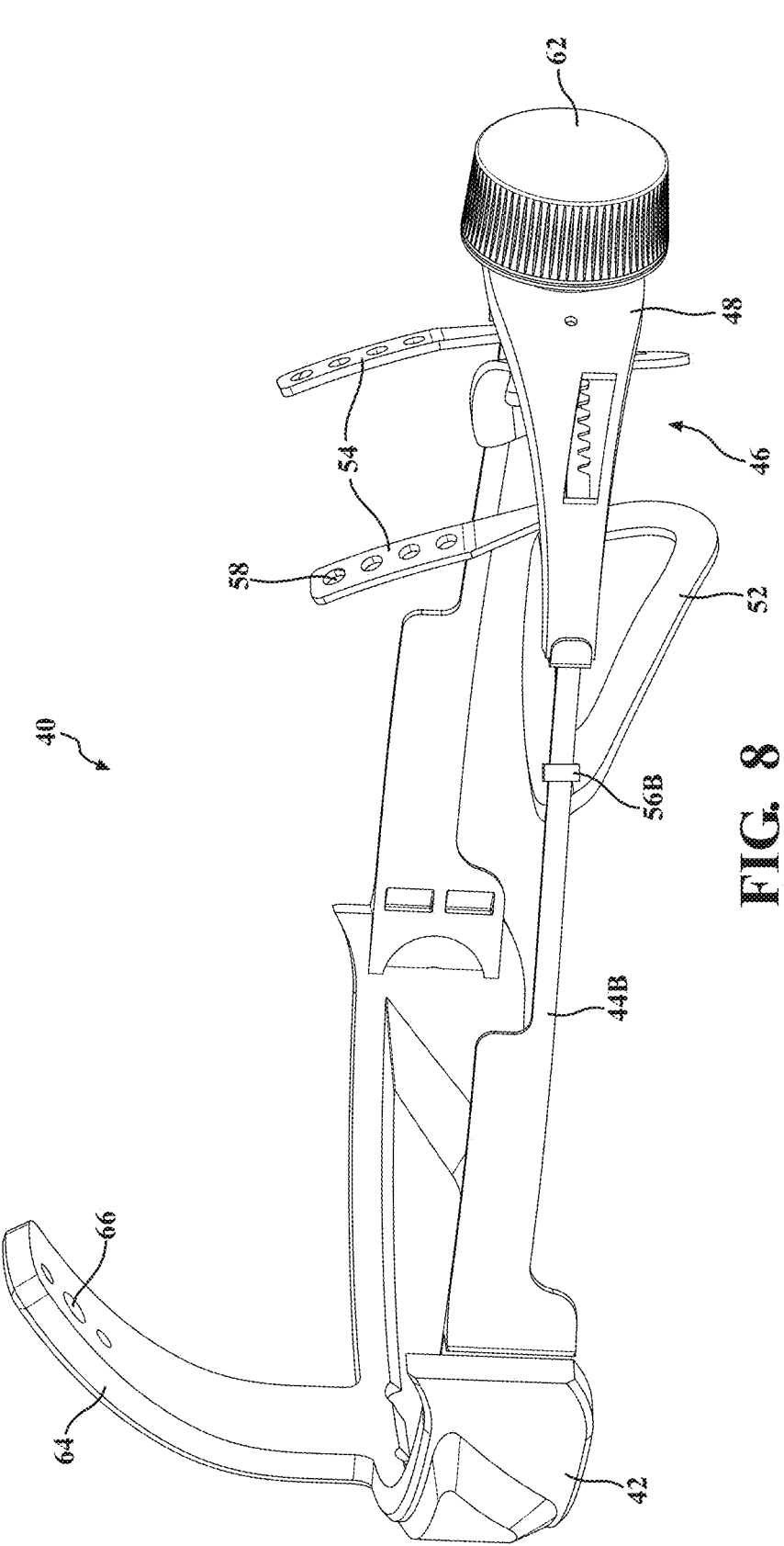
FIG. 8 is a side perspective view of the headband of FIG. 6.
Figure 9:
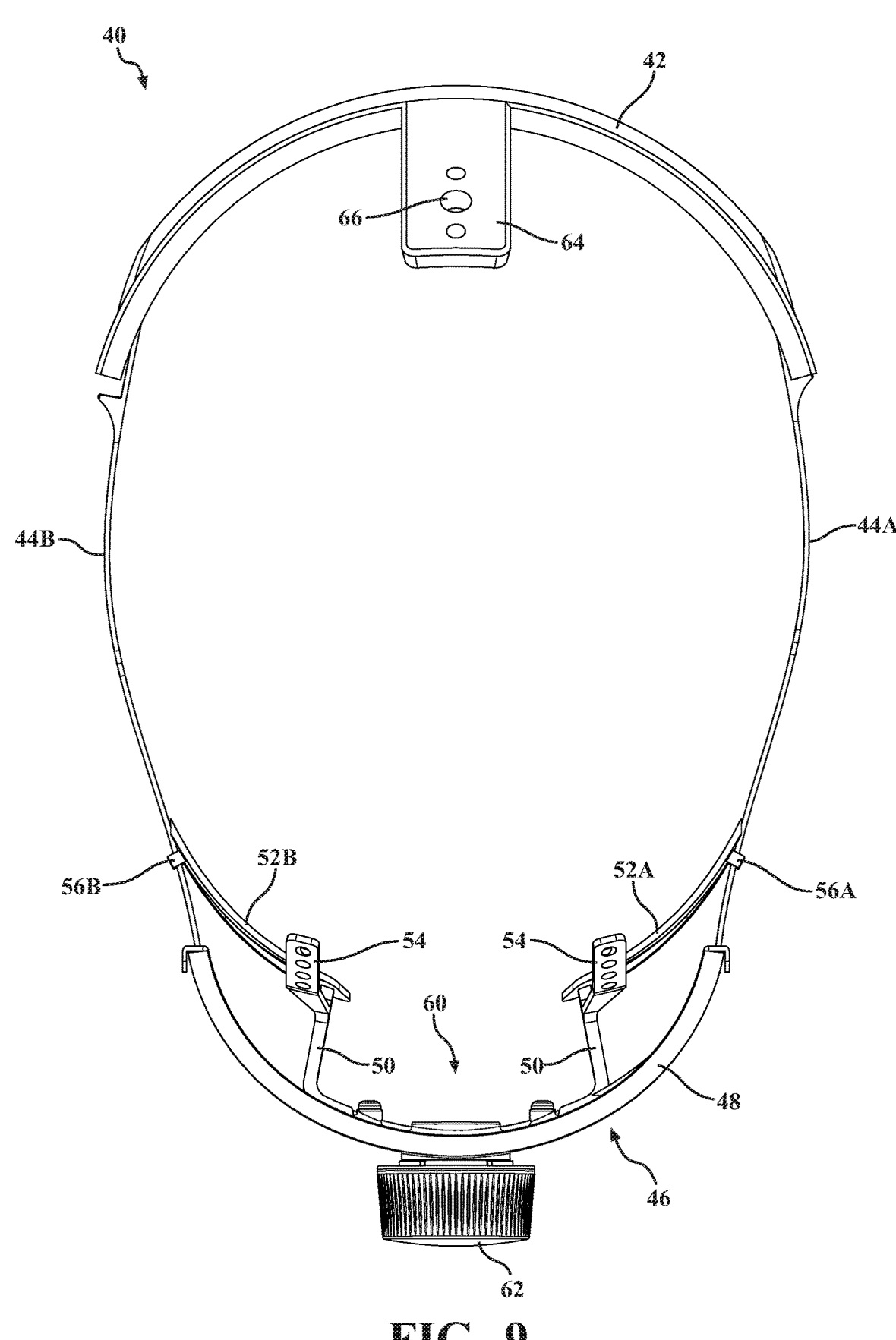
FIG. 9 is a top view of the headband of FIG. 6.

The rear portion 46 of the headband 40 may further comprise a rear mounting feature 54 for removably attaching the headband 40 to the housing 21 of the helmet 20. The mounting feature 54 may comprise a coupling feature 58, such as a plurality of apertures. As illustrated in FIG. 2B, the coupling feature 58 of the mounting feature 54 of the headband 40 may be configured to engage the complementary attachment feature 55 of the helmet 20 described above. Alternatively, the mounting feature 54 may include a coupling feature comprising a hook and loop fastener, slot, post, or similar fastener for engaging the complementary attachment feature of the helmet 20 to removably attach the headband 40 to the housing 21 of the helmet 20.

Referring back to FIGS. 2B and 3, the combination of the headband 40 and the housing 21 may be further configured to provide a hair management system that seeks to provide additional functionality and comfort for wearer's that may have longer hair and/or wear their hair in a ponytail. To accommodate individuals with longer hair, in addition to the void 60 defined by the headband 40 between the contact surface(s) 52A, 52B and the base 48 of the rear portion, the housing 21 may be shaped to define a second void 61 in the rear of the helmet 20. The void 61 may be positioned and/or configured to receive a ponytail of hair or a similar hair styling. The first void 60 defined by the headband 40 and the second void 61 defined by the housing 21 may be oriented and/or aligned relative to one another such that the combination of the first and second voids 60, 61 provide additional comfort to the user for various hair lengths and/or stylings.

The housing 21 may also include the attachment feature 55 described above for removably securing the headband 40 to the housing 21. The attachment feature 55 may comprise a hook and loop fastener, slot, post, or similar fastener mechanism corresponding to the coupling feature 58 of the mounting feature 54 of the headband 40. As illustrated in FIG. 2B, the attachment feature 55 may comprise a post or a protrusion extending from the housing 21. This may be configured to be positioned in an aperture 58 of the headband 40. Alternatively, the attachment feature 55 may comprise an aperture configured to receive a complementary post on the headband 40. The combination of the mounting feature 54 may also be configured to provide a sizing functionality. For example, as illustrated in FIG. 2B, the mounting feature 54 may comprise a plurality of apertures 58 spaced apart and sized to engage the complementary attachment feature 55 of the helmet 20 so that the rear portion 46 of the headband 40 may be spaced at varying distances from the housing 21. This may be done to accommodate the positioning of the housing 21 and/or the headband 40 relative to the wearers head, a specific type of hairdo, the location of the wearers ponytail on their head, the size of the wearer's head, and/or other related wearer preference(s).

Figure 10:
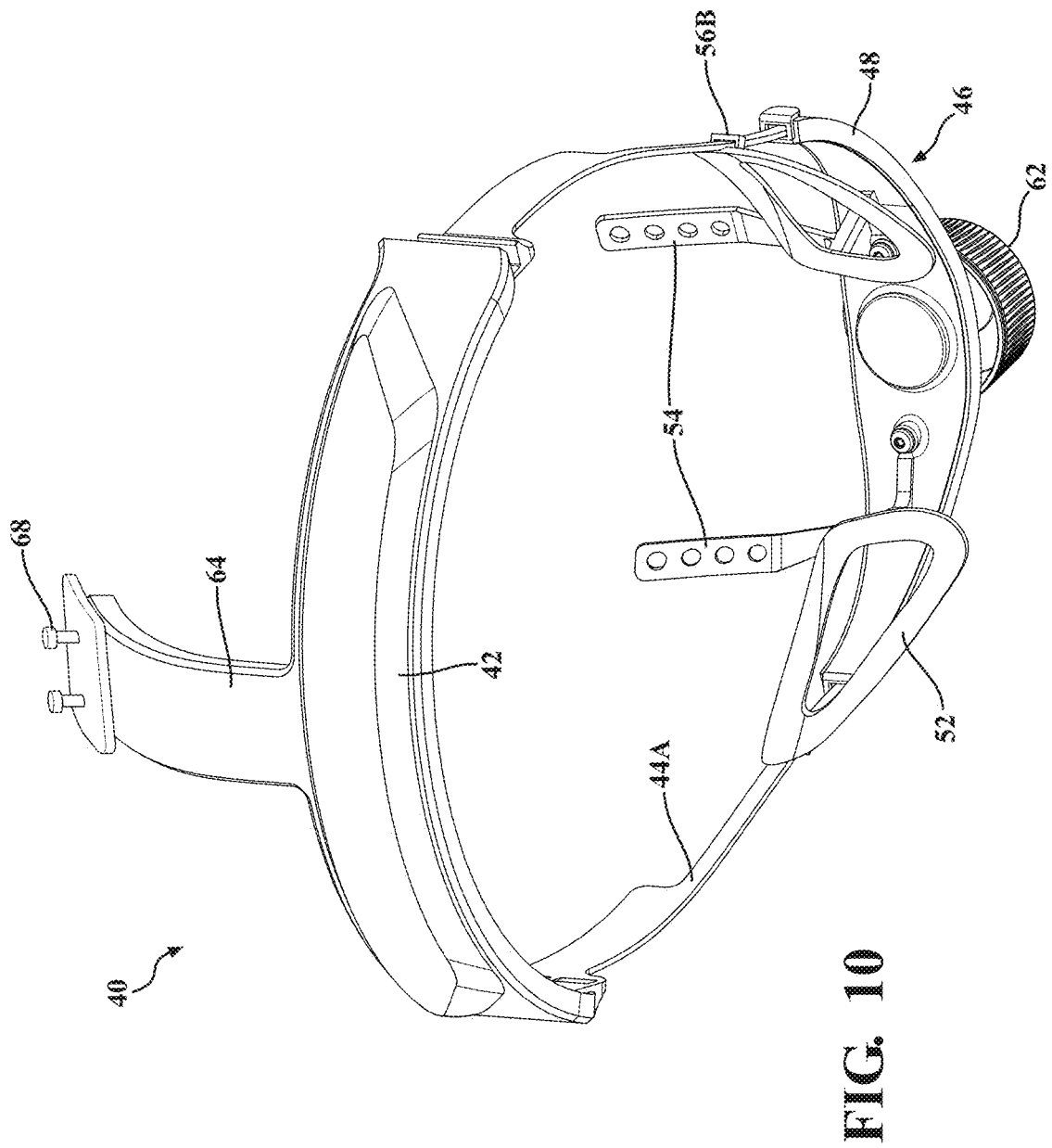
FIG. 10 is a front perspective view of an alternative headband of the surgical helmet of FIG. 2A.

FIG. 10 shows a headband 40 further comprising an alternative coupling member 68. The coupling member 68 may optionally be coupled to and or disposed on the strap 64 of the front portion 42 of the headband and configured to removably couple the head band to the surgical helmet 20, and more specifically the housing 21 of the surgical helmet 20.

Referring to FIGS. 11 to 15, an alternative configuration of a surgical helmet 120 is illustrated including the headband 40. It should be noted, that features of the helmet 120 may include any and/or all of the features illustrated and described above with reference to FIGS. 1A to 5. Common components or features in the alternative configuration of the helmet will include a leading 1 in the reference number, i.e. 21 and 121 correspond to common components including similar features and/or functions across both configuration of the surgical helmet 20, 120.

The helmet 120 may include a housing 121 and a headband 40 for supporting the housing 121 on the wearer's head. The helmet 121 may also comprise a face frame 122 defined by an upper beam 134, post(s) 124, and a lower beam 126 similar to the face frame 22 described above.

The housing 121 of the helmet may also optionally including a coupling feature 69. The coupling feature 69 may be configured to engage the correspond coupling feature 66, 68 of the headband 40. For example, the coupling feature 69 may be an aperture defined in the underside of the housing 121 and configured to engage the correspond coupling feature 68 of the headband 40 that is defined as a post. Alternatively, coupling feature 69 may be a post extending from the underside of the housing 121 and configured to engage the correspond coupling feature 66 of the headband 40 defined as an aperture in the strap 64. While reciprocal post and/or apertures configured to a create a snap of press fit are illustrated in the figures, alternative means of coupling the headband 40 to the housing 121 and/or helmet 120 are contemplated. For example, the coupling features 66, 68, 69 may be configured as hook and loop, snaps, complementary magnetic and ferromagnetic members, or similar fasteners.

Figure 11:
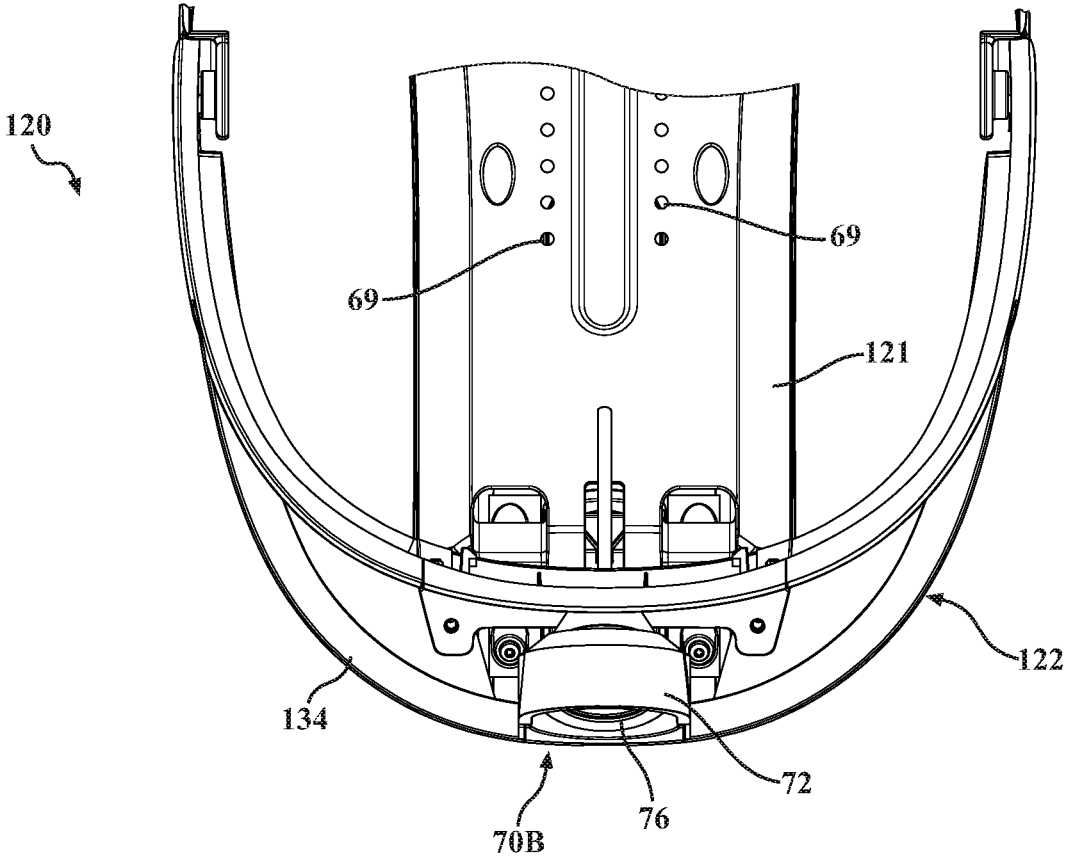
FIG. 11 is a bottom view of a surgical helmet including coupling features for attachment and adjustment of the headband of FIG. 10 to a shell of the surgical helmet.
Figure 12:
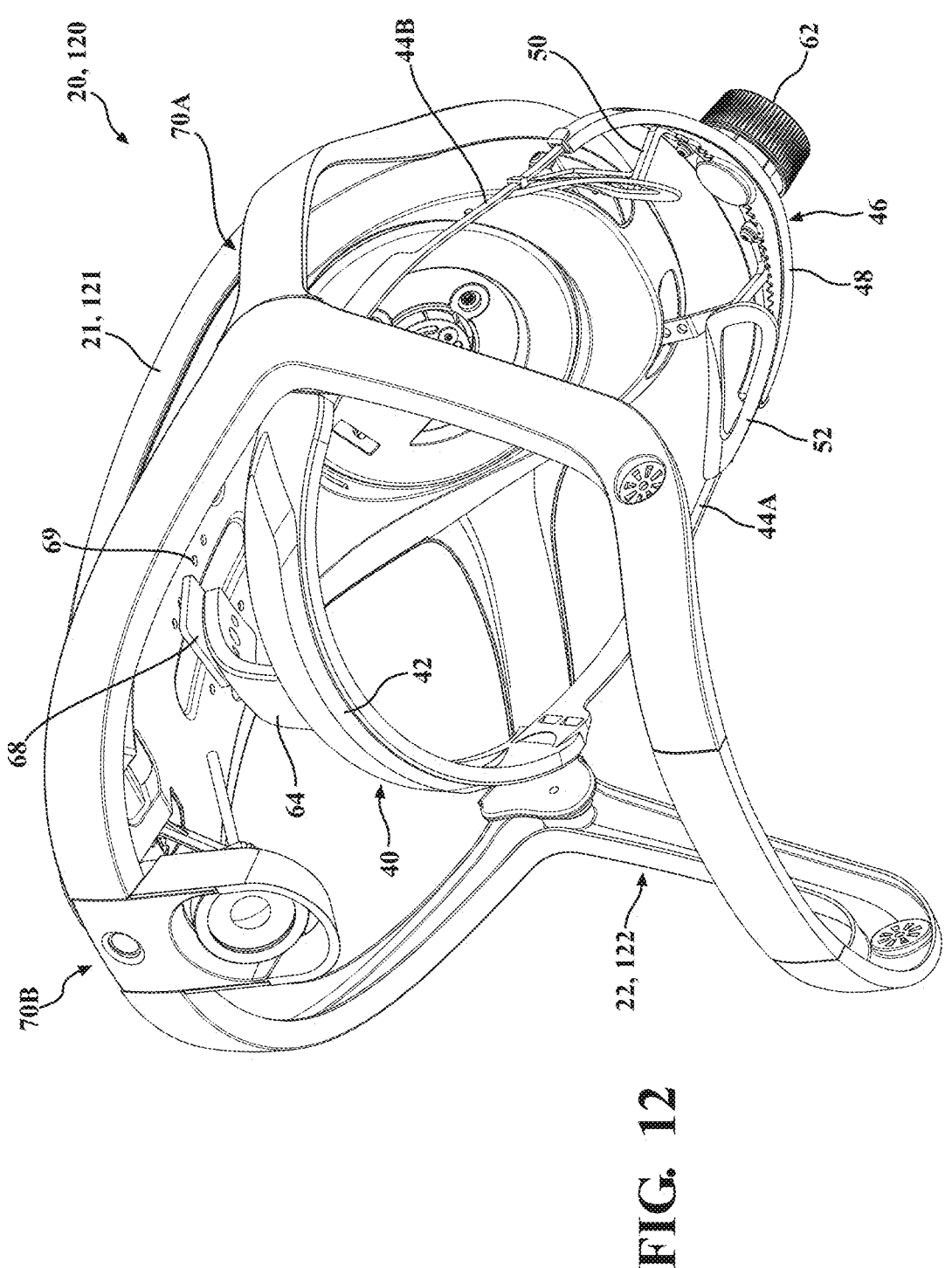
FIG. 12 is a perspective view of a surgical helmet, the surgical helmet including the headband of FIG. 10 coupled to the shell of the surgical helmet of FIG. 11.
Figure 13:
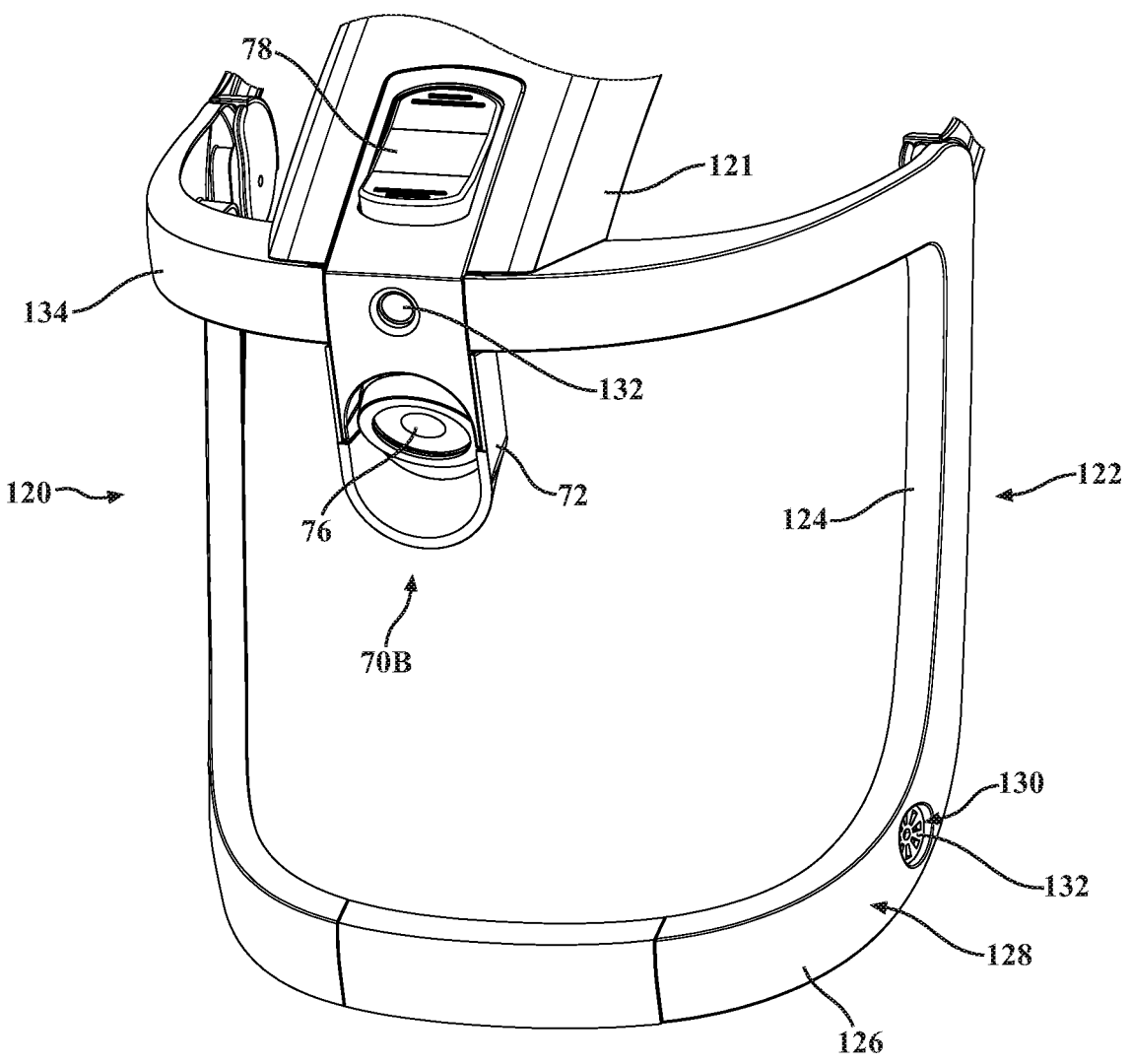
FIG. 13 is a front view of an alternative configuration of a face frame of a surgical helmet, the face frame including a surgical light and light shroud.
Figure 14:
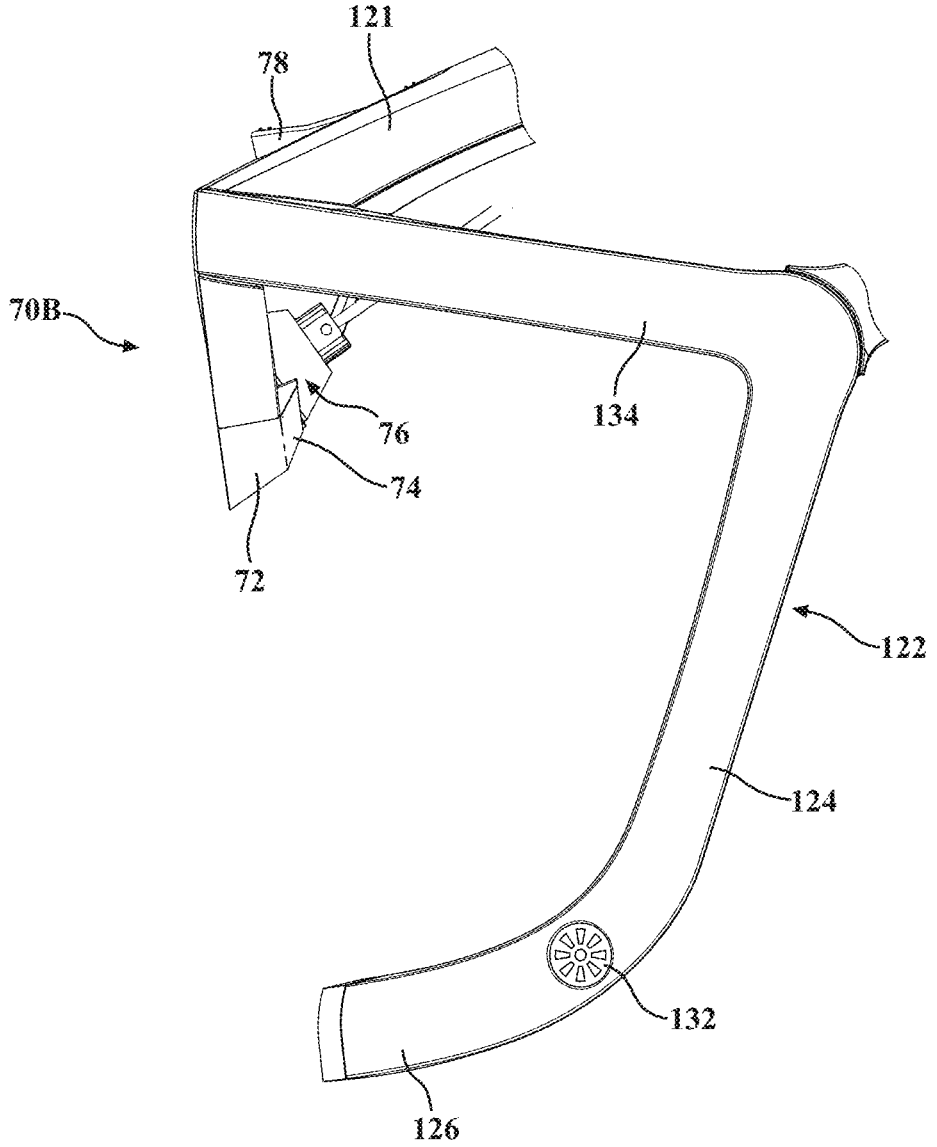
FIG. 14 is a side view of the face frame of FIG. 13, including the surgical light and light shroud.
Figure 15:
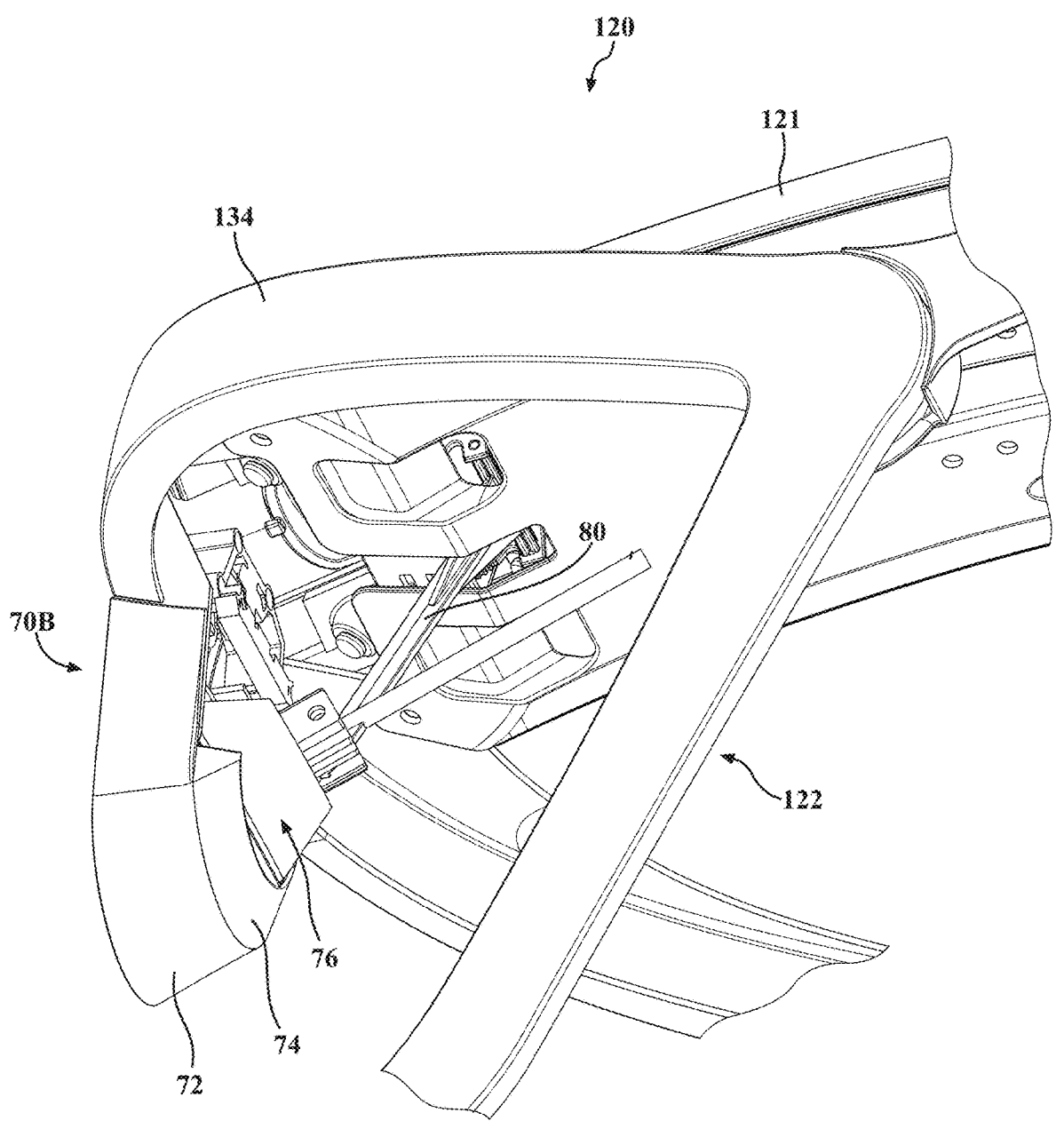
FIG. 15 is a bottom perspective view of the surgical light and light shroud of the face frame of FIG. 13
Figure 17:
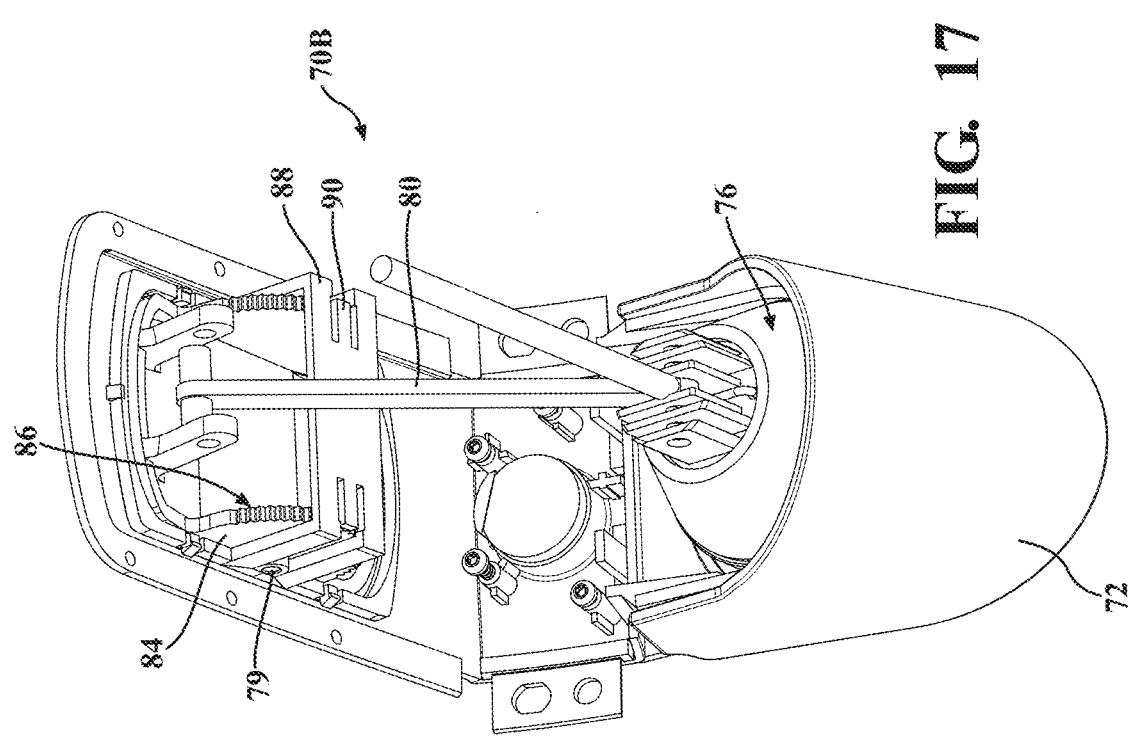
FIG. 17 is a rear perspective view of the surgical light and light shroud.
Figure 16:
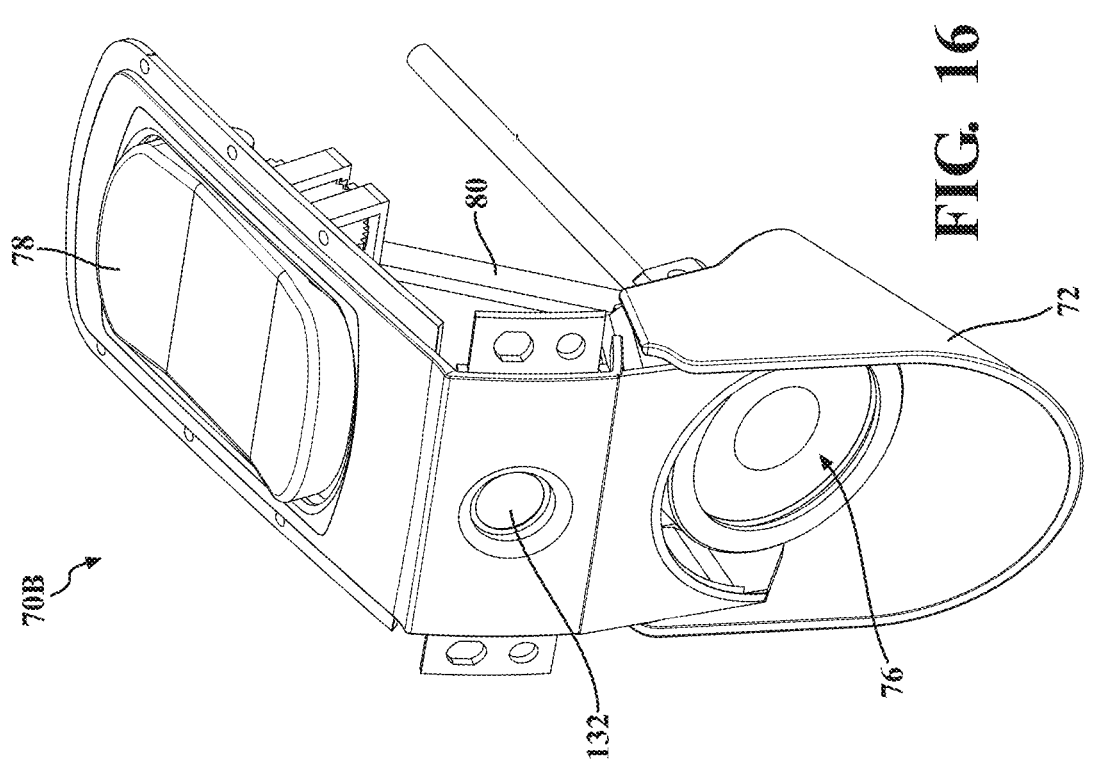
FIG. 16 is a front perspective view of the surgical light and light shroud.
Figures 18, 19:
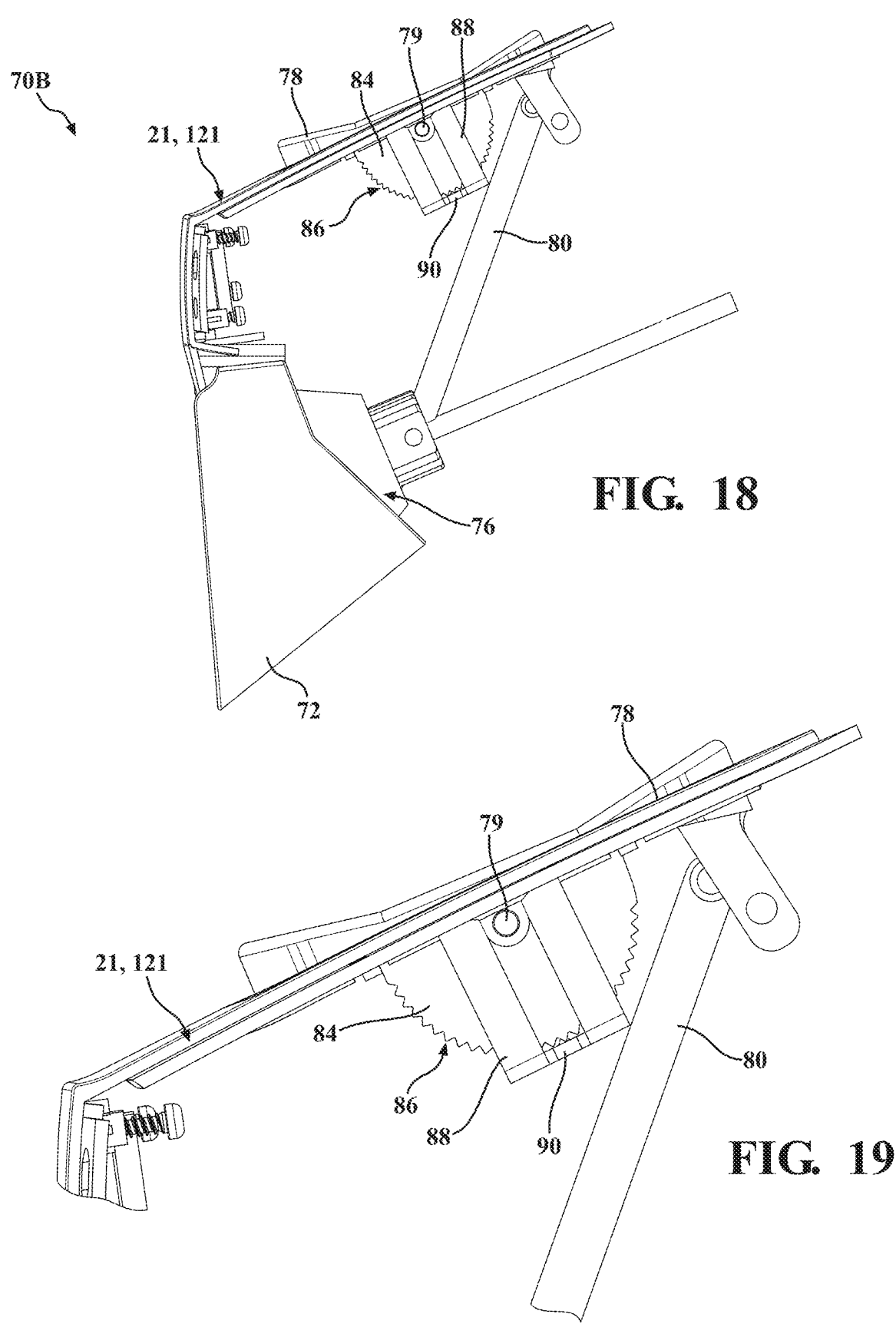
FIG. 18 is a side view of the surgical light and light shroud.
FIG. 19 is a zoomed side view of an example adjustment mechanism of the surgical light and light shroud.

Referring to FIG. 11, a plurality of coupling features 69 may be disposed on and/or spaced along the housing 121. The plurality of coupling features 69 may be incrementally spaced along the housing 121 to allow the complementary coupling feature 66, 68 of the headband 40 to be attached to the housing 121 at different locations. This will allow for the placement of the housing to be sagittally adjusted relative to the headband 40, and by extension the wearer's head to provide for additional comfort and/or functionality. For example, repositioning the housing 121 relative to the headband using the coupling features 66, 68, 69 may allow for the center of mass of the housing 121 to be more optimally placed above the wearer's head creating less strain on the wearer's neck and/or spine. Additionally, repositioning the housing 121 relative to the headband using the coupling features 66, 68, 69 may allow the user to optimize their field of vision by reducing or removing potential interferences with the wearer's vision created by the position of the housing 121 and/or the face frame 122 relative to the wearer's eyes.

Referring to FIGS. 11 to 15, the face frame 122 and the housing 121 of the surgical helmet 120 may be configured to accommodate a peripheral device 70B. The peripheral device 70B illustrated FIGS. 11 to 15 is a light assembly 70B coupled to the helmet 120 and include a light element 76. The light assembly 70B may be mounted to an outer surface of the housing 121, face frame 122, or another portion of the surgical helmet 120. The light assembly 70B may support and/or position the light element 76 in a location to the illuminate the area in view the wearer of the helmet 120. All or portions of the light assembly 70B may be removably coupled to the helmet 120. Alternatively, the light assembly 70B may be permanently affixed to and/or formed as a unitary part of the helmet 120.

The light assembly 70B may also comprise a light shroud 72 coupled to and/or disposed on the helmet 120 and/or face frame 122 to at least partially encircle the light element 76. The light shroud 72 may be spaced a distance from the periphery of the light element 76 to allow the light element 76 to move within and/or relative to the light shroud 72. The light shroud 72 may be removably coupled to the helmet 120, housing 121, and/or face frame 122. The light shroud 72 may also be separable from the other components of the light assembly 70B. The light shroud 72 may be coupled to the housing 121, and/or face frame 122 by a snap-fit, friction-fit, screw, bolt, hook and loop, and/or similar fastener. Alternatively, the light shroud 72 may be formed as a unitary part of the housing 121, and/or face frame 122 of the surgical helmet 120. The light assembly 70B may be configured to position the light element proximate and/or adjacent the face shield 18 of the surgical garment 12. The light shroud may similarly have a distal edge positioned adjacent the face shield 18 and configured to prevent any glare and/or reflection created from the light element 76 on the face shield from reflecting back into the wearer of the helmet's 120 eyes.

The light assembly 70B may further comprise a pliable member 74 that extends between the proximal end of the light shroud 72 and the light element 76 to fill any gap between the proximal end of the light shroud 72 and the light element 76. The pliable member 74 may be coupled to one of or both the light shroud 72 and/or the light element 76. The pliable member 76 covers the gap between the light shroud 72 and the light element 76 while still allowing the light element 76 to move relative to the light shroud.

Referring to FIGS. 16-19, the light assembly 70B may further comprise a control member 78 configured to reposition the light element 76. The control member may be a button, switch, or rocker. The control member 78 may be coupled to a gear 84 including a plurality of teeth 86. The control member 78 may be configured to rotate the gear 84 about a pivot 79 when the control member 78 is manipulated by the wearer.

The light assembly 70B may comprise a frame 88 in engagement with the teeth 86 of the gear 84. The frame 88 may further comprise a detent 90 that is biased to engage the teeth 86 of the gear 84 to resist the rotation of the gear 84, and by extension the control member 78, absent a force being applied to the control member 78 by the wearer.

A bracket 80 may be coupled to the control member 78 and the light element 76, with the bracket 80 configured to manipulate the position of the light element 76 based on the wearer's positioning of the control member 78.

Several examples have been described in the foregoing description. However, the examples discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical helmet for use with a surgical garment configured to define a barrier between a wearer and an external environment, the surgical helmet comprising:

a headband including a front portion, a rear portion and a pair of opposed side portions connecting the front portion to the rear portion, the headband configured to encircle a head of the wearer;

a ventilation assembly coupled to the headband, the ventilation assembly configured to draw air through the surgical garment and circulate it about the wearer;

wherein the rear portion of the headband comprises:

a base member for slidably receiving an end of each of the pair of opposed side portions of the headband;

a pair of separate contact surfaces spaced apart from one another to define a first void therebetween and configured to contact the head of the wearer, each of the pair of contact surfaces is slidably coupled to one of the side portions;

at least one support member disposed between each of the pair of contact surfaces and the base member, the at least one support member configured to offset the contact surface proximally from the base member to define a second void between each of the pair of contact surfaces and the base member of the rear portion of the headband to allow the hair to collect between the head of the wearer and the base member; and wherein the pair of contact surfaces and the support member are formed as an integral member of the base member of the rear portion of the headband.

2. The surgical helmet of claim 1, further comprising a control member disposed on the base member of the rear portion of the headband and configured to alter a circumference of the headband by moving each of the pair of opposed side portions relative to the base member of the rear portion.

3. The surgical helmet of claim 1, wherein the combination of the front portion, the rear portion, and the pair of opposed side portions define a continuous headband.

4. The surgical helmet of claim 1, wherein the first void is defined laterally between the support member of each of the pair of contact surfaces and the second void is defined sagittally between the base member and each of the pair of contact surfaces.

5. The surgical helmet of claim 1, further comprising:
   a housing of the surgical helmet, the housing coupled to the headband and configured to at least partially encircle the ventilation assembly; and
   a head lamp disposed on at least one of the housing of the surgical helmet or the headband and configured to project a beam of light distally in front of the face of the wearer of the surgical helmet.

6. The surgical helmet of claim 5, further comprising a bracket coupled to the housing of the surgical helmet and configured to at least partially encircle the head lamp, the bracket shaped to assist with directing the beam of light from the head lamp distally and away from the wearer.

7. The surgical helmet of claim 5, further comprising a shroud removably coupled to one of the surgical helmet, the housing of the surgical helmet, or a face frame of the surgical helmet; and
   wherein the shroud defines a void configured to partially surround the head lamp, the shroud shaped to assist with directing the beam of light from the head lamp distally and away from the face of the wearer.

8. The surgical helmet of claim 6, wherein the shroud comprises a distal edge and opposing proximal edge, the distal edge configured to be positioned adjacent the surgical garment; and
   a flexible member extending between the proximal edge of the shroud and a light element of the head lamp, the flexible member configured to move with the head lamp to fill a portion of the void between the proximal edge of the shroud and the housing of the head lamp to prevent beam of light from the head lamp from being directed and/or reflected toward the wearer.

9. The surgical helmet of claim 8, further comprising a rocker disposed on the housing of the surgical helmet, the rocker coupled to the housing of the head lamp and manipulatable by the wearer to move the head lamp to direct the beam of light coming from the head lamp.

10. The surgical helmet of claim 1, further comprising:
   a housing, the housing coupled to the headband and configured to at least partially encircle the ventilation assembly;
   a strap disposed on the front portion of the headband, the strap comprising at least one front mounting feature; and
   wherein the housing comprises a plurality of coupling features configured to removably engage the front mounting feature of the front portion of the headband, the plurality of coupling features incrementally spaced along the housing to provide sagittal adjustment of the front portion of the headband relative to the housing.

11. The surgical helmet of claim 10, wherein the front mounting feature comprises a post and the plurality of coupling features comprise a plurality of apertures defined in the housing and configured to receive the post and create a friction fit to removably secure the front portion of the headband to the housing.

12. The surgical helmet of claim 1, further comprising a housing, the housing coupled to the headband and configured to at least partially encircle the ventilation assembly; and
   wherein the second void defined by the rear portion of the housing and the first void defined between the pair of contact surfaces of the rear portion of the headband are aligned vertically and configured to allow the hair of the wearer to collect between the head of the wearer and the base member of the rear portion of the headband without interference from the headband or the housing.

13. A surgical helmet including an electrically powered assembly, the surgical helmet comprising:
   a housing;
   a headband for supporting the housing above a wearer's head, the headband comprising:
      a front portion;
      a pair of opposed side portions;
      a rear portion connected to the front portion by the pair of opposed side portions, the combination of the front portion, the pair of opposed side portions, and the rear portion of the headband configured to encircle a head of the wearer, the rear portion comprising:
         a base member for receiving an end of each of the pair of opposed side portions;
         a control member disposed on the base member, the control member configured to extend and retract each of the pair of opposed side portions relative to the base member to alter a circumference of the headband;
         a pair of discontinuous contact surfaces positioned on opposed sides of a midline of the headband extending between the front and rear portions and configured to contact the head of the wearer, each of the pair of contact surfaces slidably coupled to one of the side portions; and
      a support member disposed between each of the pair of contact surfaces and the base member, the support member configured to space the base member distally away from each of the contact surface defining a void between the pair of contact surfaces and the base member to allow the hair to collect between the head of the wearer and the base member; and
      wherein the pair of contact surfaces and the support member are formed as an integral member of the base member of the rear portion of the headband.

14. The surgical helmet of claim 13, wherein the void comprises a first void defined laterally between the support member of each of the pair of contact surfaces and a second void defined sagittally between the base member and each of the pair of contact surfaces.

15. The surgical helmet of claim 13, further comprising:
   a strap disposed on the front portion of the headband, the strap comprising at least one front mounting feature; and
   wherein the surgical helmet comprises a plurality of coupling features configured to removably engage the front mounting feature of the front portion of the headband, the plurality of coupling features incrementally spaced along the surgical helmet to provide sagittal adjustment of the front portion of the headband relative to the surgical helmet.

16. A surgical helmet including an electrically powered assembly, the surgical helmet comprising:

a headband comprising:

a front portion;

a pair of opposed side portions;

a rear portion connected to the front portion by the pair of opposed side portions, the combination of the front portion, the pair of opposed side portions, and the rear portion of the headband configured to encircle a head of the wearer, the rear portion comprising:

a base member for receiving an end of each of the pair of opposed side portions;

a pair of contact surfaces positioned on opposed sides of a midline of the headband extending between the front and rear portions and configured to contact the head of the wearer, the pair of contact surfaces spaced apart laterally to define a first void therebetween, each of the pair of contact surfaces slidably coupled to one of the side portions; and a support member disposed between each of the pair of contact surfaces and the base member, the support member configured to offset the base member away from the pair of contact surfaces and the wearer's head, the support member defining a second void between the pair of contact surfaces and the base member to allow the hair to collect between the head of the wearer and the base member; and wherein the pair of contact surfaces and the support member are formed as an integral member of the base member of the rear portion of the headband.

17. The surgical helmet of claim 16, further comprising a control member is disposed on the base member of the rear portion of the headband, the control member configured to manipulate a position of each of the pair of opposed side portions relative to the base member of the rear portion.

* * * * *